(12) United States Patent
Kissinger et al.

(10) Patent No.: US 10,966,646 B2
(45) Date of Patent: Apr. 6, 2021

(54) SIMPLIFIED BLOOD SAMPLING DEVICE AND METHOD

(71) Applicant: Phlebotics, Inc., West Lafayette, IN (US)

(72) Inventors: Candice B. Kissinger, West Lafayette, IN (US); Peter Kissinger, West Lafayette, IN (US)

(73) Assignee: Phlebotics, Inc., West Lafayette, IN (US)

( * ) Notice: Subject to any disclaimer, the term of this patent is extended or adjusted under 35 U.S.C. 154(b) by 203 days.

(21) Appl. No.: 15/301,255

(22) PCT Filed: Apr. 2, 2015

(86) PCT No.: PCT/US2015/023985
§ 371 (c)(1),
(2) Date: Sep. 30, 2016

(87) PCT Pub. No.: WO2015/157074
PCT Pub. Date: Oct. 15, 2015

(65) Prior Publication Data
US 2017/0014060 A1    Jan. 19, 2017

Related U.S. Application Data

(60) Provisional application No. 61/976,079, filed on Apr. 7, 2014.

(51) Int. Cl.
*A61B 5/155*    (2006.01)
*A61B 5/15*    (2006.01)

(52) U.S. Cl.
CPC .......... *A61B 5/155* (2013.01); *A61B 5/15003* (2013.01); *A61B 5/150221* (2013.01); *A61B 5/150229* (2013.01); *A61B 5/150992* (2013.01); *A61B 5/150366* (2013.01); *A61B 2560/0475* (2013.01); *A61B 2560/0487* (2013.01)

(58) Field of Classification Search
CPC ................ A61B 5/155; A61B 5/15003; A61B 5/150229; A61B 5/150992
See application file for complete search history.

(56) References Cited

U.S. PATENT DOCUMENTS

| 4,077,395 | A | 3/1978 | Woolner | |
|---|---|---|---|---|
| 4,258,717 | A * | 3/1981 | Bisera | A61B 5/02158 600/486 |
| 5,066,283 | A | 11/1991 | Skrabal | |
| 6,200,264 | B1 | 3/2001 | Satherley et al. | |

(Continued)

FOREIGN PATENT DOCUMENTS

WO    2013/148616 A1    10/2013

OTHER PUBLICATIONS

International Search Report and Written Opinion issued by the ISA/US, Commissioner for Patents, dated Aug. 5, 2015, for International Application No. PCT/US2015/023985; 7 pages.

(Continued)

*Primary Examiner* — Daniel L Cerioni
*Assistant Examiner* — Raymond P Dulman
(74) *Attorney, Agent, or Firm* — Faegre Drinker Biddle & Reath LLP

(57) ABSTRACT

An apparatus and method for collecting a predetermined amount of blood or other fluid using an automated sampling system is provided.

14 Claims, 16 Drawing Sheets

(56) References Cited

U.S. PATENT DOCUMENTS

| | | | |
|---|---|---|---|
| 8,348,844 B2 | 1/2013 | Kurijan et al. | |
| 2001/0031932 A1 | 10/2001 | Blake et al. | |
| 2004/0019313 A1* | 1/2004 | Childers | A61M 1/1696 604/5.01 |
| 2005/0281713 A1 | 12/2005 | Hampsch | |
| 2006/0079809 A1 | 4/2006 | Goldberger | |
| 2006/0102091 A1 | 5/2006 | Kissinger | |
| 2006/0188407 A1* | 8/2006 | Gable | G06F 19/00 604/19 |
| 2008/0209357 A1* | 8/2008 | Vasta | A61M 1/16 715/771 |
| 2010/0192686 A1* | 8/2010 | Kamen | A61M 1/16 73/290 R |
| 2010/0217154 A1* | 8/2010 | Deshmukh | A61B 5/155 600/575 |
| 2011/0313318 A1* | 12/2011 | Rule | A61B 5/14532 600/581 |
| 2012/0088309 A1 | 4/2012 | Peters et al. | |
| 2013/0023792 A1* | 1/2013 | Markey | A61B 5/15003 600/578 |
| 2013/0086998 A1* | 4/2013 | Lee | B01L 3/5027 73/863.24 |
| 2013/0261499 A1* | 10/2013 | Kissinger | A61B 5/155 600/573 |

OTHER PUBLICATIONS

European Patent Office; Extended European Search Report; Application No. 15776609.8; dated Nov. 6, 2017.
International Preliminary Report on Patentability received for PCT Patent Application No. PCT/US2015/023985, dated Oct. 20, 2016, 6 pages.

* cited by examiner

SIMPLIFIED BLOOD SAMPLING DEVICE AND METHOD

CROSS-REFERENCE TO RELATED APPLICATIONS

This application is a U.S. national phase of International Application No. PCT/US2015/023985, titled "SIMPLIFIED BLOOD SAMPLING DEVICE AND METHOD," filed Apr. 2, 2015, which claims priority from U.S. Provisional Application Ser. No. 61/976,079, titled "SIMPLIFIED BLOOD SAMPLING DEVICE AND METHOD," filed Apr. 7, 2014, the entire contents of both disclosures are hereby incorporated by reference in their entireties.

FIELD OF THE DISCLOSURE

The disclosure relates to a method for use in treating patients and performing biomedical research, and in particular to a method for automatically collecting a predetermined amount of blood or other fluid from patients for diagnostic or research purposes.

BACKGROUND AND SUMMARY OF THE DISCLOSURE

Automated blood sampling ("ABS") is a method of automatically collecting serial blood or other fluid samples from a patient for diagnostic or research purposes. ABS reduces the trauma associated with multiple "sticks" (insertion of a needle into a vein or artery) during the repeated blood sampling that is necessary to monitor disposition of drug treatments. This may have particular relevance in sampling blood or other fluids from very young infants, such as those in neonatal or pediatric intensive care, who may have little blood to spare.

ABS has benefits in research, such as during Phase 1 and Phase 2 Clinical Trials (in association with electrocardiography, blood pressure recording, and body temperature monitoring). Automating the process of blood or fluid sampling potentially allows sampling to be done with greater volume and temporal accuracy (i.e. the collection of particular sample volumes at specific times), allows for the use of less human personnel, and reduces the amount of fluid wasted compared to manual methods of acquiring the same samples and data. Automated blood sampling may also reduce the risk of infections, including nosocomial infections. Automated blood sampling also eliminates labor for manual assurance of catheter patency.

ABS units may also be provided in a portable embodiment. In some embodiments, the ABS unit includes a battery or other portable power source. The use of a portable ABS allows for greater mobility of the patient during sample collection. Patients may be able to go about daily activities, such as eating meals, sending mails, reading a book, and walking to a restroom, while attached to an ABS unit. Greater mobility and fewer sticks may lead to reduced stress. Stress involves the release of various hormones, and such hormones may affect the samples being collected in both human and non-human studies. U.S. Pat. No. 8,052,617, directed to a PORTABLE SAMPLING OR TESTING DEVICE AND METHOD FOR PHARMACOKINETICS AND PHYSIOLOGY STUDIES, and U.S. patent application Ser. No. 13/431,377, published as U.S. Patent Application Publication 2013/0261499, directed to a CARTRIDGE FOR AUTOMATED BLOOD SAMPLING SYSTEM, disclose apparatus and methods for conducting automated blood sampling, the teachings of each are herein incorporated by reference in their entireties.

Biomedical research techniques, such as infusion, in vivo microdialysis, in vivo ultrafiltration, in vivo electrochemistry, and electrocardiology study the performance of living organs, such as the brain, heart, circulatory system, muscles, etc. These techniques also require connections between one or more external devices and one or more sensors or implants in the body. Examples of devices include syringe pumps, fraction collectors, electrometers, vacuum sources, light sources, and potentiostats. Examples of implants include infusion cannulae, ultrafiltration probes, microdialysis probes, electrodes, and biosensors.

In typical fluid collection systems, an operator must make multiple selections from a menu to set-up and begin the testing protocol. In complex and sometimes chaotic medical care environments, such as intensive care units, critical care units, neonatal intensive care units, and emergency department rooms, the use of simple, repeatable procedures is desired to reduce the occurrence of errors. In addition, typical blood sampling procedures require time for a health care provider to set up any test and/or manually withdraw samples for testing. Improvements in the foregoing are desired.

The present disclosure provides an apparatus and method for collecting a fluid sample from a subject for a test. In one exemplary embodiment, the test subject is an adult human. In another exemplary embodiment, the subject is a human child. As used herein, "test" may comprise collection of a fluid sample, as in automated blood sampling, sampling of another body fluid, or parallel acquisition of an electronic signal, such as during blood pressure or electrocardiogram monitoring. The fluid sample collected may be used in medical or clinical analysis of the patient for diagnostic or research purposes. In one embodiment, the sample collection and analysis are provided as a part of neonatal, pediatric or adult intensive care of the patient, including but not limited to military intensive care. In another embodiment, the sample collection and analysis are provided as a part of a personalized medicine regime or treatment. Example of personalized medicine treatment include, but are not limited to, measuring the circulating concentration of an administered drug or tracking the patient's chemical response to a drug. In still another embodiment, the sample collection and analysis are provided as a component of biomedical research. Those of skill in the art will recognize that the sample collection and analysis may also be provided as part of other medical or clinical processes.

In an exemplary embodiment, the disclosure provides a method for conducting an automated fluid collection. The method comprises: connecting the test subject to the automated fluid sampling device. The fluid sampling device includes: a pump being moveable in a first direction to draw fluid into the pump and a second direction to expel fluid from the pump; a reservoir in fluid communication with the pump, the reservoir having a first opening and a second opening; a first conduit fluidly connecting the reservoir to a first fluid fitting configured to fluidly connect the cartridge to tubing having a distal end inserted into the subject; a second conduit fluidly connecting the reservoir to a second fluid fitting configured to connect the cartridge to a sample collection component; and a third conduit fluidly connecting the reservoir to a third fluid fitting configured to connect the cartridge to a sterile fluid supply. The pump is configured to move in the first direction and second direction in response to movement of a portion of the fluid sampling device and the fluid conduits are configured such that a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit, each valve having an open state and a closed state; and wherein the fluid sampling device includes a controller for controlling the pump and valve.

The method further comprises activating a predetermined routine on the automated fluid sampling device, said predetermined routine including the steps of: opening the first valve, and moving the pump in the first direction to draw sample fluid through the first conduit and into the reservoir; thereby forming a sample fluid/sterile fluid interface; opening the second valve, and moving the pump in the second direction to force a sample fluid from the reservoir through the second conduit to the sample collection component, the sample collection component collecting a predetermined amount of fluid; re-opening the first valve, and moving the pump in the second direction to force the sterile fluid out of the first fluid fitting, thereby flushing the first conduit; re-opening the second valve, and moving the pump in the second direction to force the sterile fluid out of the second fluid fitting, thereby flushing the second conduit and the sample collection component, and opening the third valve, and moving the pump in the first direction to draw the sterile fluid through the third fluid fitting and into the pump through the first opening of the third conduit. The activating step is performed by depressing a single button on the automated fluid sampling device.

In an exemplary embodiment, the disclosure provides an apparatus for conducting an automated fluid collection. The apparatus includes: a pump being moveable in a first direction to draw fluid into the pump and a second direction to expel fluid from the pump; a reservoir in fluid communication with the pump, the reservoir having a first opening and a second opening; a first conduit fluidly connecting the reservoir to a first fluid fitting configured to fluidly connect the cartridge to tubing having a distal end inserted into the subject; a second conduit fluidly connecting the reservoir to a second fluid fitting configured to connect the cartridge to a sample collection component; and a third conduit fluidly connecting the reservoir to a third fluid fitting configured to connect the cartridge to a sterile fluid supply. The pump is configured to move in the first direction and second direction in response to movement of a portion of the fluid sampling device and the fluid conduits are configured such that a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit, each valve having an open state and a closed state; and wherein the fluid sampling device includes a controller for controlling the pump and valve.

The automated fluid sampling device further includes a user interface comprising a single button. Upon activation of the button, a predetermined routine is activated including the steps of: opening the first valve, and moving the pump in the first direction to draw sample fluid through the first conduit and into the reservoir; thereby forming a sample fluid/sterile fluid interface; opening the second valve, and moving the pump in the second direction to force a sample fluid from the reservoir through the second conduit to the sample collection component, the sample collection component collecting a predetermined amount of fluid; reopening the first valve, and moving the pump in the second direction to force the sterile fluid out of the first fluid fitting, thereby flushing the first conduit; re-opening the second valve, and moving the pump in the second direction to force the sterile fluid out of the second fluid fitting, thereby flushing the second conduit and the sample collection component, and opening the third valve, and moving the pump in the first direction to draw the sterile fluid through the third fluid fitting and into the pump through the first opening of the third conduit. In a more particular embodiment, the automated fluid sampling device further includes a cover covering at least a portion of the user interface. In an even more particular embodiment, at least a portion of the cover covers the single button.

In an exemplary embodiment, the disclosure provides a method for conducting an automated fluid collection into multiple vials. The method comprises (a) providing an automated fluid sampling device, the automated fluid sampling device comprising: a pump being moveable in a first direction to draw fluid into the pump and a second direction to expel fluid from the pump; a reservoir in fluid communication with the pump, the reservoir having a first opening and a second opening; a first conduit fluidly connecting the reservoir to a first fluid fitting configured to fluidly connect the cartridge to tubing having a distal end inserted into the subject; a second conduit fluidly connecting the reservoir to a second fluid fitting configured to connect the cartridge to a sample collection component containing first and second sample collection vessels; and a third conduit fluidly connecting the reservoir to a third fluid fitting configured to connect the cartridge to a sterile fluid supply, wherein the pump is configured to move in the first direction and second direction in response to movement of a portion of the fluid sampling device when the cartridge is operably connected to the fluid sample device and the fluid conduits are configured such that when the cartridge is operably connected to the fluid sampling device, a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit, each valve having an open state and a closed state; and wherein the fluid sampling device includes a controller for controlling the pump and valve.

The method further comprises (b) connecting the distal end of the tubing to the subject; (c) opening the first valve, and moving the pump in the first direction to draw sample fluid through the first conduit and into the reservoir; thereby forming a sample fluid/sterile fluid interface; and (d) opening the second valve, and moving the pump in the second direction to force sample fluid from the reservoir through the second conduit to the first sample vessel positioned in the sample collection component. The method further comprises (e) moving the pump in the second direction to force sample fluid from the reservoir through the second conduit to the second sample vessel positioned in the sample collection component. The method further comprises (f) re-opening the first valve, and moving the pump in the second direction to force the sterile fluid out of the first fluid fitting, thereby flushing the first conduit; (g) re-opening the second valve, and moving the pump in the second direction to force the sterile fluid out of the second fluid fitting, thereby flushing the second conduit and the sample collection component, and (h) opening the third valve, and moving the pump in the first direction to draw the sterile fluid through the third fluid fitting and into the pump through the first opening of the third conduit, wherein steps (c)-(h) are executed by the controller.

In a more particular embodiment, the controller repeats steps (c)-(h) a plurality of times in succession. In another more particular embodiment, the method further comprises prior to step (c): actuating the pump to fill the pump with the sterile fluid; opening second valve, and actuating the pump to fill the reservoir and the second conduit with the sterile fluid; opening the first valve and actuating the pump to fill the first conduit with the sterile fluid; coupling the tubing to the first fluid fitting; opening the first valve, and actuating the pump to draw a first amount of fluid from the tubing; and opening the first valve, and actuating the pump to return the first amount of blood through the tubing to the subject. In still another more particular embodiment, the first and second sample collection vessels are different sizes.

In an exemplary embodiment, the disclosure provides an apparatus for conducting an automated fluid collection into multiple vials. In a more particular embodiment, the first and second sample collection vessels are different sizes.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

The disclosure is explained in greater detail below in reference to the figures. In the figures.

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to a sample or testing device for intensive care medicine, pharmacokinetics and physiology studies, it should be understood that the features disclosed herein may have application to collection of other types of samples.

Figure 1:
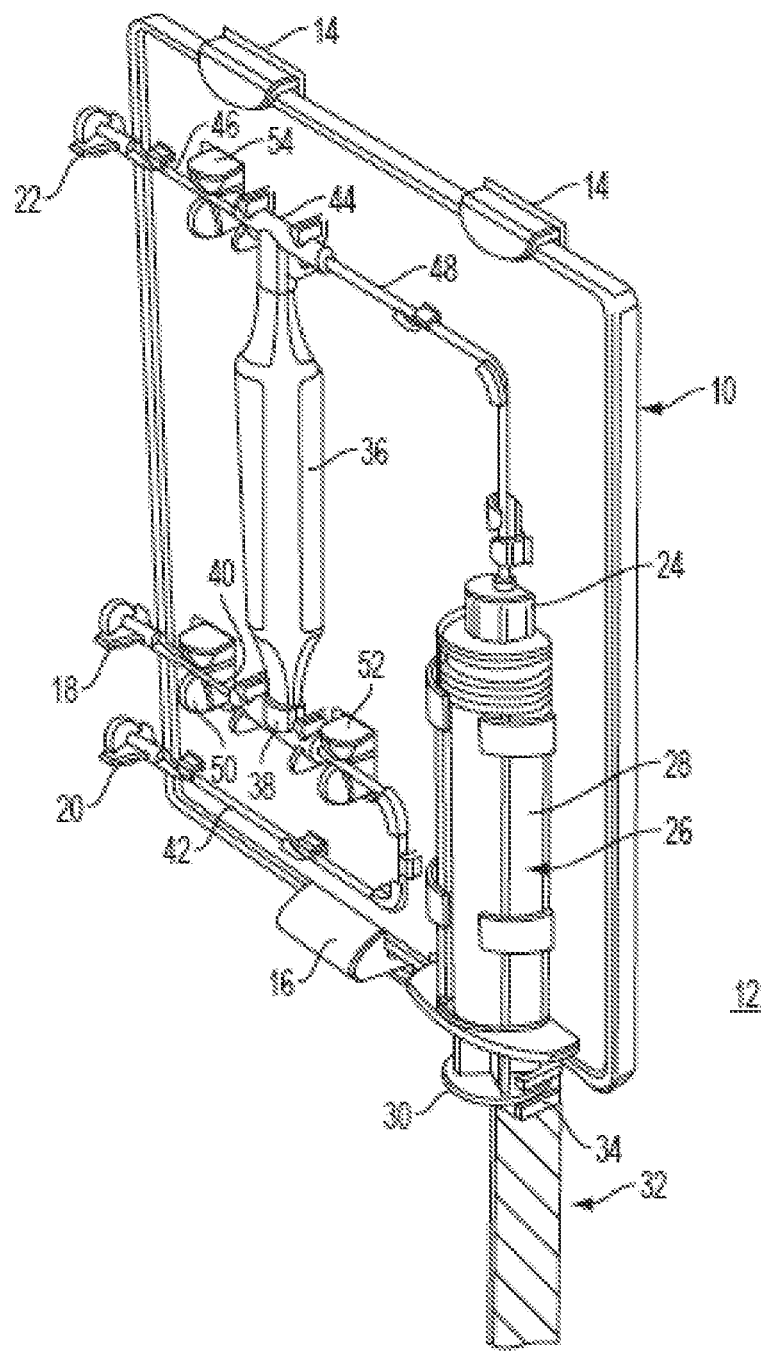
FIG. 1 shows an illustrative ABS cartridge attached to a portion of an ABS apparatus.

Referring to FIG. 1, an illustrative ABS cartridge 10 is shown attached to a portion of an ABS apparatus 12. In one exemplary embodiment, cartridge 10 is attached to ABS apparatus 12 using hooks 14 and latch 16. In the illustrated embodiment, cartridge 10 is inserted into hooks 14, latch 16 is depressed, cartridge 10 is pushed in toward ABS apparatus 12 and latch 16 snaps into position. In another embodiment, cartridge 10 is attached to ABS apparatus 12 using a plurality of hooks 14. In still another embodiment, cartridge 10 is attached to ABS apparatus 12 using a plurality of latches 16. Other suitable methods of removably attaching cartridge 10 to ABS apparatus 12, including but not limited to grooves, snaps, and rotatable clasps may also be used.

Cartridge 10 includes a plurality of connectors. In the exemplary embodiment illustrated in FIG. 1, first connector 18 connects cartridge 10 to a catheter conduit, which has a distal end inserted into the test subject from which the sample is to be collected. Although the test subject from whom the sample is to be collected in one exemplary embodiment is a human, in other embodiments fluid samples may be taken from other animals. Second connector 20 connects cartridge 10 to a sample collection container or fraction collector for collecting and storing samples. Third connector 22 connects cartridge 10 to a saline bag or other physiologically compatible solution, such as, but not limited to Ringer's solution. In another exemplary embodiment, syringe connector 24 connects cartridge 10 to syringe pump 26. In still another exemplary embodiment, syringe pump 26 is provided as part of cartridge 10. As illustrated, connectors 18, 20, 22, 24 are fluid fittings. In one exemplary embodiment, connectors 18, 20, 22, 24 are leak-free connections such as Luer lock style connectors. Exemplary Luer lock connectors are Luer-Lok™ connectors available from Becton Dickinson & Co., Franklin Lakes, N.J. Other suitable fluid fittings may also be used.

In the exemplary embodiment illustrated in FIG. 1, syringe pump 26 is provided as part of cartridge 10. Syringe pump 26 includes barrel 28 and plunger 30. ABS apparatus 12 includes syringe mechanism 32. Syringe mechanism connector 34 connects syringe mechanism 32 to plunger 30 such that movement of syringe mechanism 32 moves plunger 30. In the exemplary embodiment illustrated in FIG. 1, connector 34 attaches above and below one end of plunger 30. Other connections are also contemplated. For example, plunger 30 may include a groove into which connector 34 is inserted, or a portion of plunger 30 and connector 34 may comprise a key and slot that allow plunger 30 to move in response to movement from syringe mechanism 32. In one exemplary embodiment, syringe pump 26 may comprise the Culex ABS syringe drive manufactured by Bioanalytical Systems, inc. of West Lafayette, Ind. In other embodiments, syringe pump 26 is another means for moving fluid including, but not limited to, a reciprocal piston pump, a peristaltic pump, or a vacuum or pressure source.

In another exemplary embodiment, syringe pump 26 is not provided as part of cartridge 10, but is connected to cartridge 10 through syringe connector 24 and to a portion of ABS apparatus 12 through syringe mechanism connector 34.

Cartridge 10 includes fluid reservoir 36. In the exemplary embodiment illustrated in FIG. 1, reservoir 36 is a container into which fluid can be received and dispensed. In another exemplary embodiment, fluid reservoir 36 is an enlarged section of conduit or tubing. In still another exemplary embodiment, fluid reservoir 36 is an extended length of conduit or tubing. In still yet another exemplary embodiment, fluid reservoir is integrally formed with cartridge 10.

A first end of reservoir 36 is fluidly connected to first intersection or T connector 38. T connector 38 fluidly connects reservoir 36 to first connector 18 through catheter conduit 40 and second connector 20 through collector conduit 42.

A second end of reservoir 36 is fluidly connected to second intersection or T connector 44. T connector 44 fluidly connects reservoir 36 to third connector 22 through reservoir conduit 46 and syringe pump 26 through syringe conduit 48.

Although the exemplary embodiment of cartridge 10 illustrated in FIG. 1 shows reservoir 36 as a vertically oriented container attached to first T connector 38 below reservoir 36 and attached to second T connector 44 above reservoir 36, other orientations are also contemplated, including but not limited to horizontal connections of first and second T connectors 38, 44 with reservoir 36 and reversing the positions of first and second T connectors 38, 44.

In the exemplary embodiment illustrated in FIG. 1, catheter conduit 40 is routed through first valve 50, collector conduit 42 is routed through second valve 52, and reservoir conduit 46 is routed through third valve 54. In one embodiment, valves 50, 52, 54 are operably connected to ABS apparatus 12.

Figure 2C:
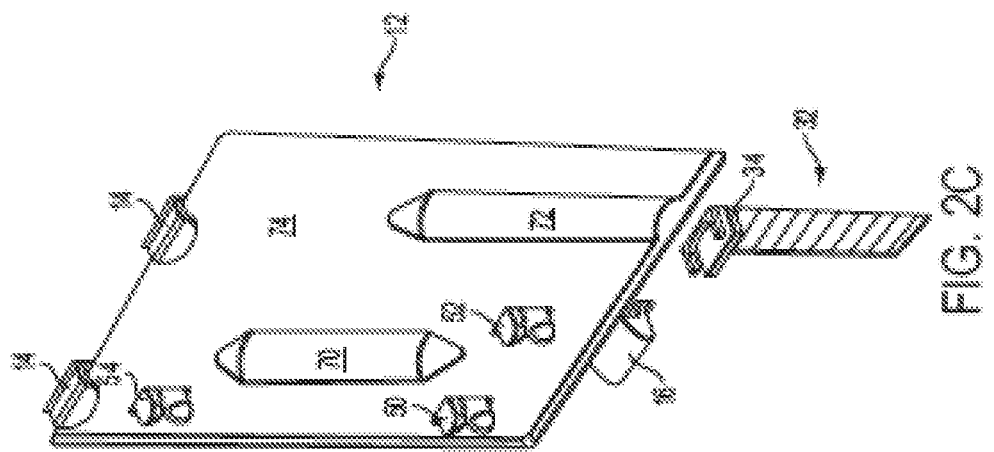
FIGS. 2A-2C show an exploded view of the ABS cartridge and ABS apparatus portion of FIG. 1.
Figure 2B:
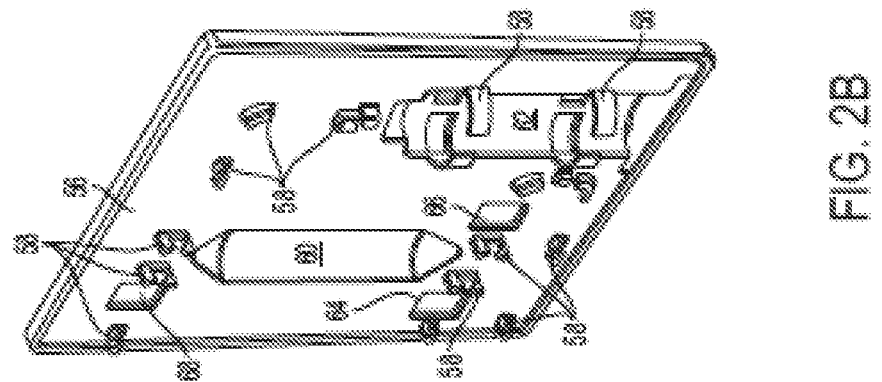
Figure 2A:
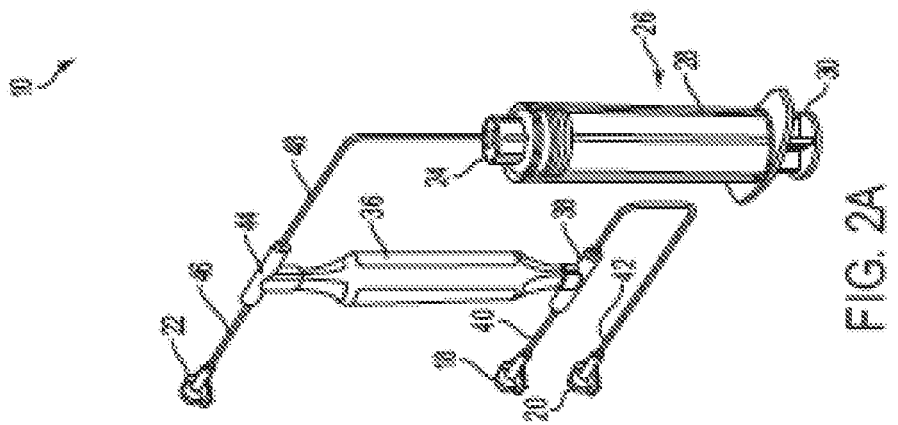

Referring next to FIG. 2, an exploded view of cartridge 10 and ABS apparatus 12 of FIG. 1 is illustrated. FIG. 2A illustrates a portion of one exemplary embodiment of cartridge 10 including connectors 18, 20, 22, 24, syringe pump 26, reservoir 36, T connectors 38, 44, and conduit 40, 42, 46, 48. FIG. 2B illustrates another portion of the exemplary embodiment of cartridge 10 including cartridge frame 56. FIG. 2C illustrates a portion of one exemplary embodiment of ABS apparatus 12 for receiving cartridge 10 including hooks 14, latch 16, syringe mechanism 32, and valves 50, 52, and 54.

In the exemplary embodiment illustrated in FIGS. 1 and 2, cartridge frame 56 includes a plurality of snap and routing supports 58. Snap and routing supports 58 support cartridge components on frame 56. The plurality of snap and routing supports 58 may include clamps, guides, snaps, and supports. As shown in FIG. 2B, snap and routing supports 58 may be formed as part of cartridge frame 56. In another embodiment, snap and routing supports 58 may be attached to cartridge frame 56. Snap and routing supports 58 may be formed from a plastic or other polymeric material. Those of skill in the art will recognize that other materials may also be used. In one embodiment, snap and routing supports 58 support at least one of conduit 40, 42, 46, 48. In another embodiment, snap and routing supports 58 support at least one of T connectors 38, 44. In still another embodiment, snap and routing supports 58 support syringe barrel 28.

Referring to FIG. 2B, in one exemplary embodiment, cartridge frame 56 includes recesses 60, 62, for receiving reservoir 36 and syringe pump 26. In another exemplary embodiment, at least one of recesses 60, 62 are cut-outs.

In the exemplary embodiment illustrated in FIG. 2B, cartridge frame 56 includes first valve window 64 for receiving valve 50, second valve window 66 for receiving valve 52, and third valve window 68 for receiving valve 54 from ABS apparatus 12. In another embodiment, more than one valve may be positioned in a window.

In one exemplary embodiment, valves 50, 52, and 54 are pinch valves that fit around conduits 40, 42, 46 and restrict or prevent fluid flow through conduits 40, 42, 46 in a closed state and allow fluid flow through conduits 40, 42, 46 in an open state. In one embodiment, valves 50, 52, and 54 include rod-like elements that fit around conduits 40, 42, 46. In the open state, the rod-like elements are positioned to allow fluid to flow through conduits 40, 42, 46. In the closed state, a force is applied to a first of the rod-like elements causing it to move toward the second of the rod-like elements, squeezing the conduits 40, 42, 46 between the rod-like elements and restricting or preventing fluid flow. In another embodiment, force is applied to both of the rod-like elements. Force may be applied to the rod-like elements through the use of a motor and cam, a linear actuator, a pneumatic actuator, a solenoid, or other suitable methods.

In another exemplary embodiment, valves 50, 52, 54 are telescoping style pinch valves. Telescoping style pinch valves have an open state that allows fluid flow through conduits 40, 42, 46 and a closed state in which a valve element is driven from ABS apparatus 12 into contact with a conduit 40, 42, 46 and against a corresponding stationary element of cartridge frame 56 positioned opposite the conduit 40, 42, 46 from the driven valve element to restrict or prevent fluid flow through the conduit 40, 42, 46.

Other suitable fluid control means can be used in place of the illustrated valves. For example, first valve 50 and second valve 52 may be replaced by a single three-way valve. Additionally, valves 50, 52, 54 may be in-line valves. In another embodiment, syringe pump 26 is connected to syringe conduit 48 connects syringe pump 26 to reservoir 36 through a three way connector with catheter conduit 40 and collector conduit 44 in place of first T connector 38. Other suitable valves may also be used.

In another exemplary embodiment, some elements of cartridge 10 are integrally formed with cartridge frame 56. In one embodiment, at least one of reservoir 36, connectors 18, 20, 22, 24, syringe barrel 28, T connectors 38, 44, and snap and routing supports 58 are formed as part of cartridge frame 56. In another embodiment, at least one of conduits 40, 42, 46, 48 is at least partially formed as part of cartridge frame 56 and valves 50, 52, 54 control flow by applying a force to a portion of conduit 40, 42, 46, 48 causing the conduit to deform and restrict or prevent fluid flow. In still another embodiment, at least one of reservoir 36, conduit 40, 42, 46, 48, connectors 18, 20, 22, 24, syringe barrel 28, and T connectors 38, 44 are integrally formed together and secured to frame 56 prior to cartridge 10 being operably connected to ABS apparatus 12.

Referring to FIG. 2C, in one exemplary embodiment, ABS apparatus 12 includes recesses 70, 72, for receiving reservoir and syringe pump recesses 60, 72. In another exemplary embodiment, at least one of recesses 70, 72 directly receives reservoir 36 or syringe pump 26. In the embodiment illustrated in FIG. 2C, ABS apparatus 12 includes cartridge recess 74 for receiving cartridge 10. Cartridge 10 is secured in recess 74 by hooks 14 and latch 16.

In one exemplary embodiment, cartridge 10 and ABS apparatus 12 cooperate to allow installation of cartridge 10 into ABS apparatus 12 in only one orientation. In the embodiment illustrated in FIGS. 1 and 2, recesses 70, 72 will receive cartridge 10 in only one orientation, and syringe mechanism 32 will only receive plunger 30 in the same orientation. Other methods of allowing installation in only one orientation are also contemplated. For example, in another embodiment, cartridge frame 56 and cartridge recess 74 are shaped to only allow installation of cartridge 10 in one orientation. In still another embodiment, cartridge frame 56 is shaped so that hooks 14 and latch 16 only engage cartridge frame 56 in one orientation.

Figure 3:
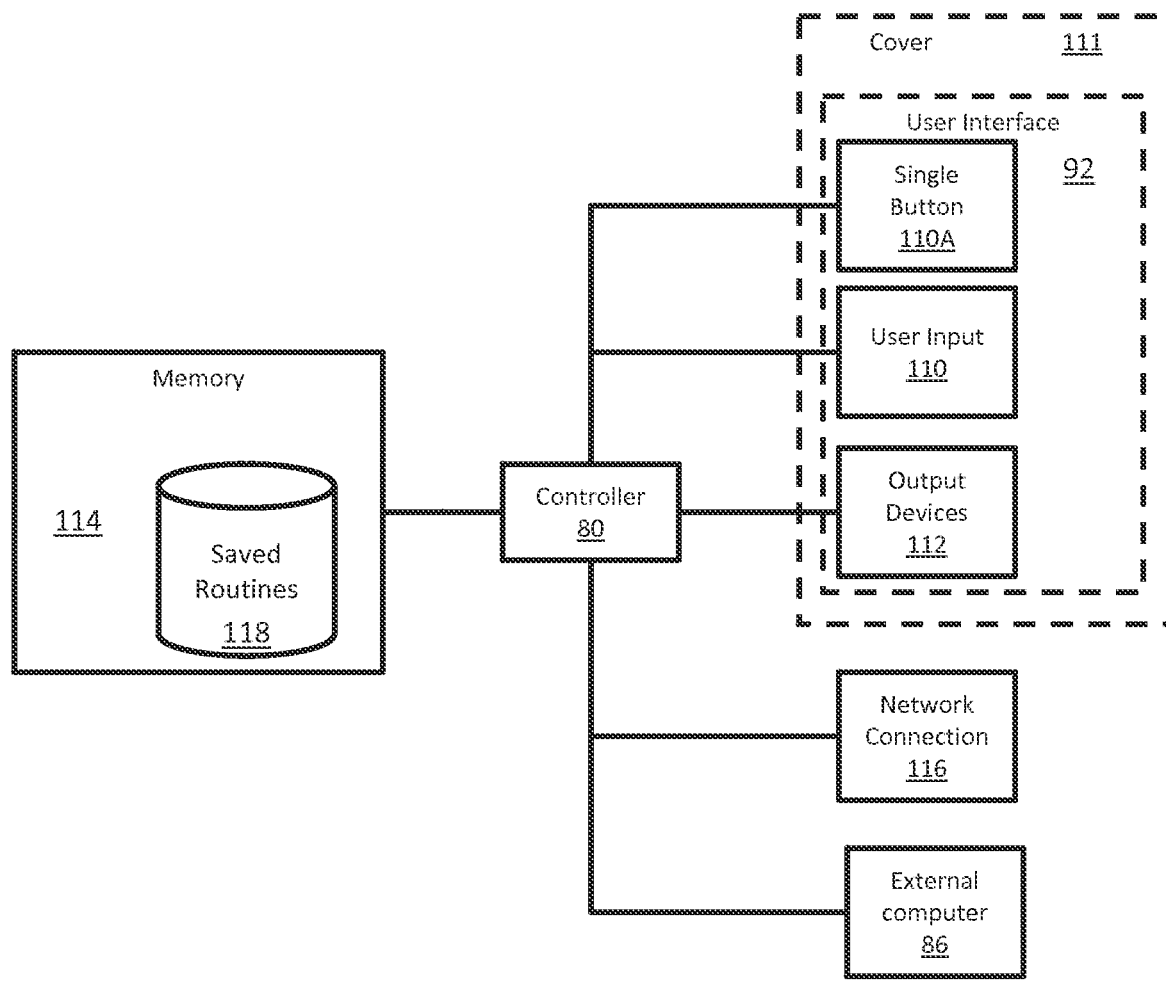
FIG. 3 illustrates an exemplary controller of the ABS apparatus of FIG. 1.
Figure 8:
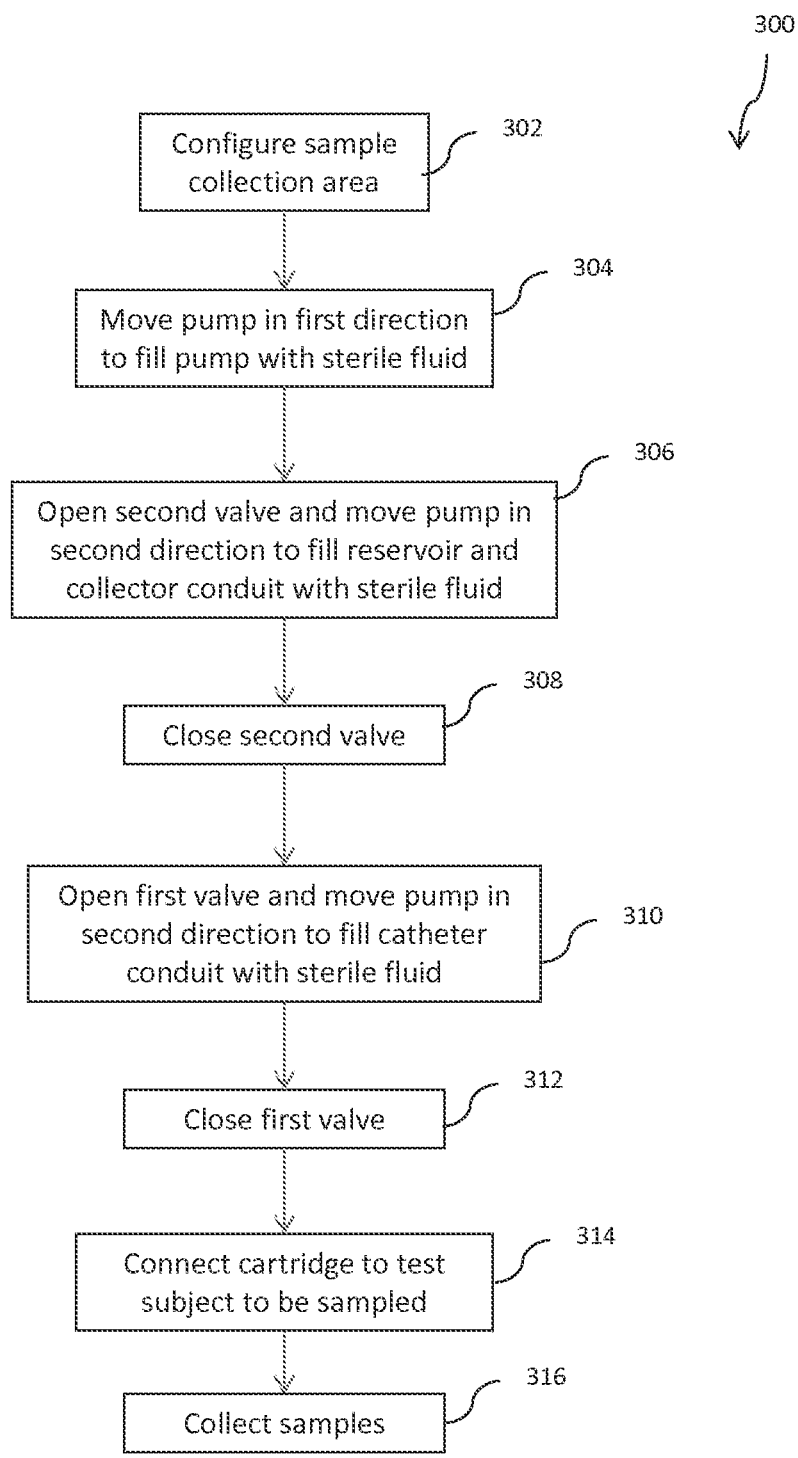
FIG. 8 illustrates an exemplary processing sequence for preparing the ABS apparatus of FIG. 7 for sampling.

Referring next to FIG. 3, when installed in ABS apparatus 12, cartridge 10 cooperates with ABS apparatus 12 to provide automated fluid sampling. ABS apparatus 12 includes controller 80, which is operatively connected to valves 50, 52, 54, syringe mechanism 32, and sample fraction collector 82. An exemplary controller is illustrated in FIG. 8. Controller 80 may be a single controller or multiple controllers. Controller 80 may implement programming implemented as electrical circuits, software being executed by a processing unit, a combination thereof, or any other suitable configuration of software and/or software enabled hardware. In one embodiment controller 80 comprises a computer chip with embedded software code. In another embodiment, controller 80 is operably connected with user interface 92. In one embodiment, user interface 92 includes input member 110 and output members 112. Exemplary input members 110 include buttons, switches, keys, a touch display, a keyboard, a mouse, and other suitable devices for providing information to controller 80. Exemplary output members 112 include lights, a display (such as a touch screen), printer, speaker, visual devices, audio devices, tactile devices, and other suitable devices for presenting information to an operator. In one embodiment, a cover 111 is provided for user interface 92. In another embodiment controller 80 operably transfers information to and receives information from an external computer 86.

Figure 6:
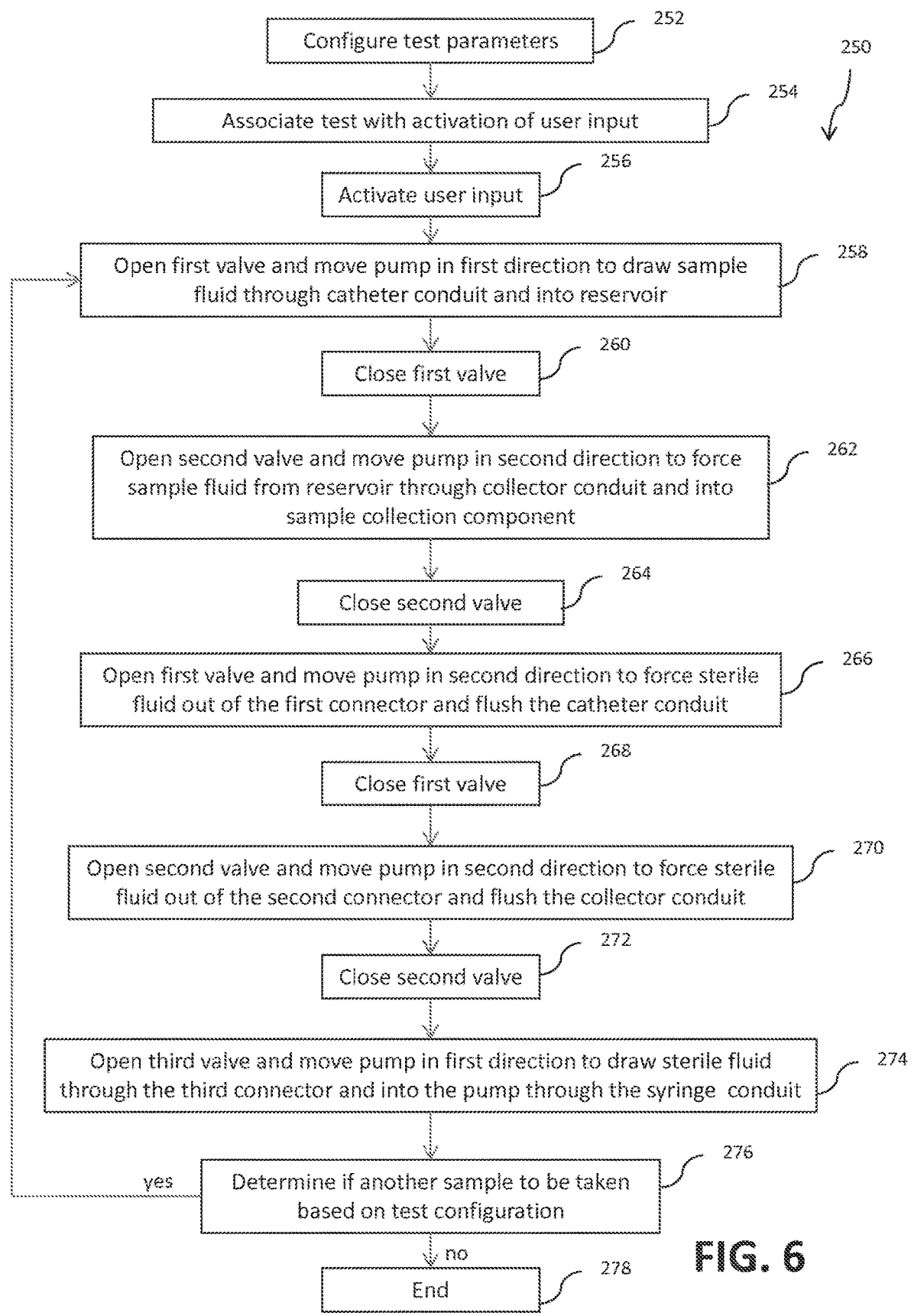
FIG. 6 illustrates an exemplary processing sequence for taking samples using an ABS apparatus and ABS cartridge.

In one exemplary embodiment, user input 110 includes a single button 110A (see FIG. 4A) Activation of single button 110A may be used to start an automatic fluid collection, such as automatic fluid collection sequence 250 (see FIG. 6). Single button 110A is activated to start an automatic fluid collection by depressing single button 110A a single time.

In some embodiments, use of a single button 110A to start an automatic fluid collection reduces operator errors by restricting the choice of tests or testing protocols to a single selection. By using a single button 110A to start the automatic fluid collection, the operator does not need to be trained in how to program or set-up a new test or even make a selection from multiple tests, minimizing the ability of the operator to select the wrong test. This may be of particular importance when selecting between testing protocols having the same or similar testing sample size, testing frequency, or sample collection types. Use of a single button 110A allows for a simpler user interface 92. In one exemplary embodiment, user interface 92 may include only single button 110A. In another exemplary embodiment, a portion of user interface 92 visible to the patient from whom samples are being withdrawn includes only the single button 110A. These and similar embodiments allow for a clean and unobtrusive user interface.

In addition, use of single button 110A to start an automatic fluid collection reduces the amount of time necessary to set up and run each test for a patient by eliminating the need for an operator to work through one or more menus to set up the test. Rather, the test is configured and loaded on the machine ahead of time, such that the operator can start the test with a single press of the single button 110A.

In one exemplary embodiment, at least a portion of user interface 92 is covered by a cover 111. In some embodiments, cover 111 is a transparent and/or flexible material that allows a user to see output members 112 and interact with user input members 110, including single button 110A. In some embodiments, cover 111 is cleanable with standard cleaning supplies, which allows for cleaning of a portion ABS apparatus 88 (see FIGS. 4A-4C) touched by a user without damaging ABS apparatus 88. In some embodiments, cover 111 is a removable, or disposable cover that can be changed at regular intervals to maintain a clean and/or disinfected surface user to interact with ABS apparatus 88.

In another embodiment, controller 80 includes memory 114. Memory is a computer readable medium and may be a single storage device or may include multiple storage devices, located either locally with controller 80 or accessible across a network. Computer-readable media may be any available media that may be accessed by controller 80 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by controller 80. In one embodiment, controller 80 communicates data, status information, or a combination thereof to a remote device for analysis. In another embodiment, memory may further include operating system software, such as WINDOWS operating system available from Microsoft Corporation of Redmond Wash. Memory further includes communications software if computer system has access to a network through a network connection 116, such as a local area network, a public switched network, a CAN network, and any type of wired or wireless network. Any exemplary public switched network is the Internet. Exemplary communications software includes e-mail software, internet browser software. Other suitable software which permit controller 80 to communicate with other devices across a network may be used.

In one exemplary embodiment, controller 80 controls the status of first valve 50 to control flow through catheter conduit 40, controls the status of second valve 52 to control flow through collector conduit 42, controls the status of third valve 54 to control flow through reservoir conduit 46; controls the movement of syringe pump 26 in a first direction drawing fluid into barrel 28 and a second direction forcing fluid from barrel 28; and instructs a sample fraction collector 82 to either receive fluid samples in vials 84 or to pass the fluid into a drain. In another embodiment, controller 80 is operatively connected to external computer 86.

Figure 4C:
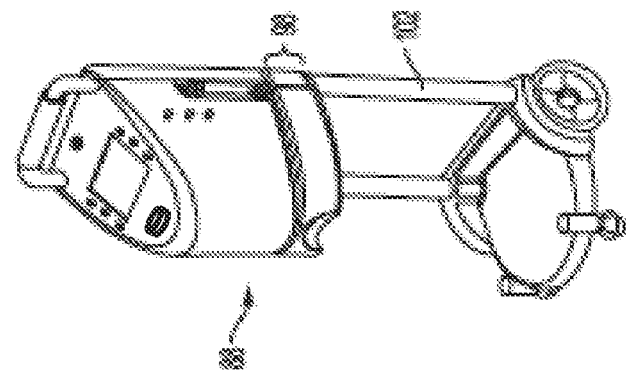
FIGS. 4A-4C show several views of an illustrative ABS apparatus with an ABS cartridge installed.
Figure 4B:
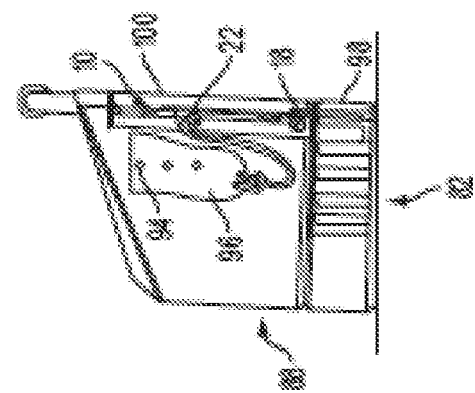
Figure 4A:
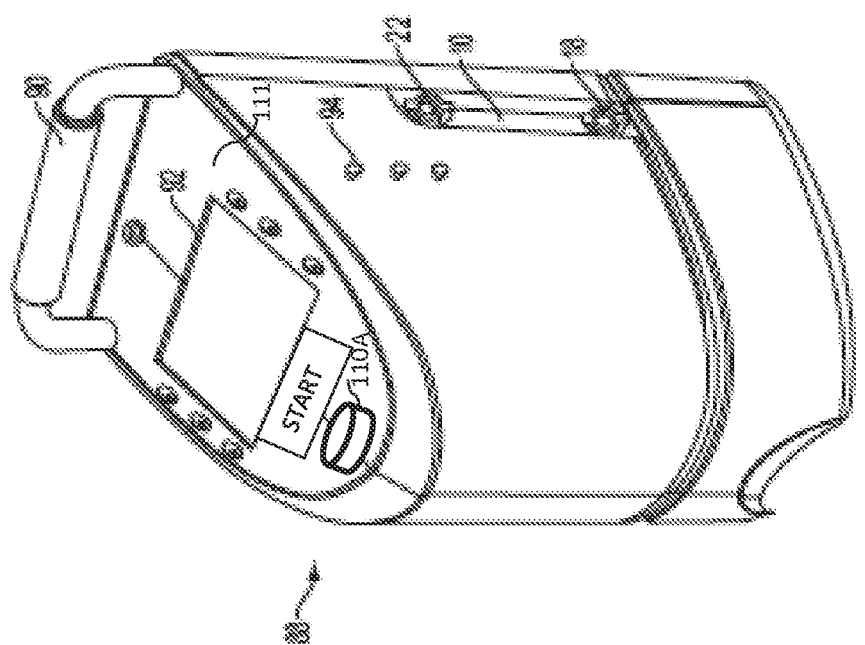

Referring next to FIG. 4, several views of an illustrative ABS apparatus are provided. FIG. 4A illustrates a perspective view of the front of an ABS apparatus 88. The exemplary ABS apparatus 88 in FIG. 4A includes handle 90 with a soft touch cover, user interface 92, and hooks 94 for attaching saline bag 96 or other physiologically compatible solution. First connector 18 and third connector 22 of cartridge 10 can be seen extending out the side of ABS apparatus 88.

Sample collection area 98 is provided in the bottom of ABS apparatus 88. In one embodiment, sample collection area may be refrigerated using Peltier cooling. In another embodiment, sample collection area 98 includes instruments for analyzing collected samples, such as for point of care testing, near patient testing, or nursing stations. Exemplary instruments for analyzing collected samples include the Cobas c and other point of care, bedside testing and near patient systems available from Roche Diagnostics, Indianapolis, Ind., the i-STAT(R) System available from Abbott Laboratories, Abbott Park, Ill., and point of care systems available from Siemens healthcare Diagnostics Inc., Tarrytown, N.Y. Other suitable instruments for analyzing collected samples, such as but not limited to mass spectrometers, may also be used. In yet another embodiment, sample collection area stores samples in vials or cartridges for later testing and analysis. In still yet another embodiment, samples may be deposited on or absorbed in a matrix such as cellulose, open foam polymer, or ceramics from which the sample will later be retrieved. In another embodiment, samples are stored as dried blood samples on Guthrie cards.

As shown in the exemplary embodiment illustrated in FIG. 4B, saline bag 96 can be attached to hook 94 and fluidly connected to third connector 22. In FIG. 4B, ABS apparatus 88 includes back panel 100. Back panel 100 may be removed from ABS apparatus 88, cartridge 10 may be installed, and back panel 100 may be replaced with access to first connector 18 and third connector 22 of cartridge 10 provided on the side of ABS apparatus 88.

As shown in FIG. 4C, ABS apparatus 88 may be provided on wheeled stand 102. In the exemplary embodiment illustrated in FIG. 4C, the sample collection area 98 is removable from ABS apparatus 88 when ABS apparatus 88 is attached to wheeled stand 102.

As shown in FIG. 4C, user interface 92 includes user input 110. User interface 92 is illustratively covered by cover 111.

Although the position and orientation of components of cartridge 10 and ABS apparatus 12 have been illustratively described, those of skill in the art will recognize that other suitable positions and orientations may be used. In some embodiments, the test subject from which the sample is taken from may influence the design.

In one embodiment, cartridge 10 and ABS apparatus 12 may include a wheeled stand to allow the test subject to remain ambulatory while testing. In another embodiment for testing very young infants, cartridge 10 and ABS apparatus 12 have components with smaller volumes than for embodiments for testing adults. In still another exemplary embodiment, ABS apparatus 12 including a portable electric power supply is incorporated into a wheel neonatal intensive care unit (NICU) isolette or incubator or an intensive care unit (ICU) bed to enable sampling to continue while a patient is moved between rooms. In yet still exemplary embodiment, ABS apparatus 12 capable is incorporated as a part of exercise physiology devices, including but not limited to treadmills and stationary bicycles, for stress tests such as stress electrocardiograms, and evaluation of athletes, patients, or members of the military. In another exemplary embodiment, ABS apparatus 12 is incorporated into a military long range pallet system used to air transport battle casualties.

Other suitable designs depending on the subject to be tested may also be used, including those exemplified in U.S. Pat. No. 8,052,617.

Figure 5:
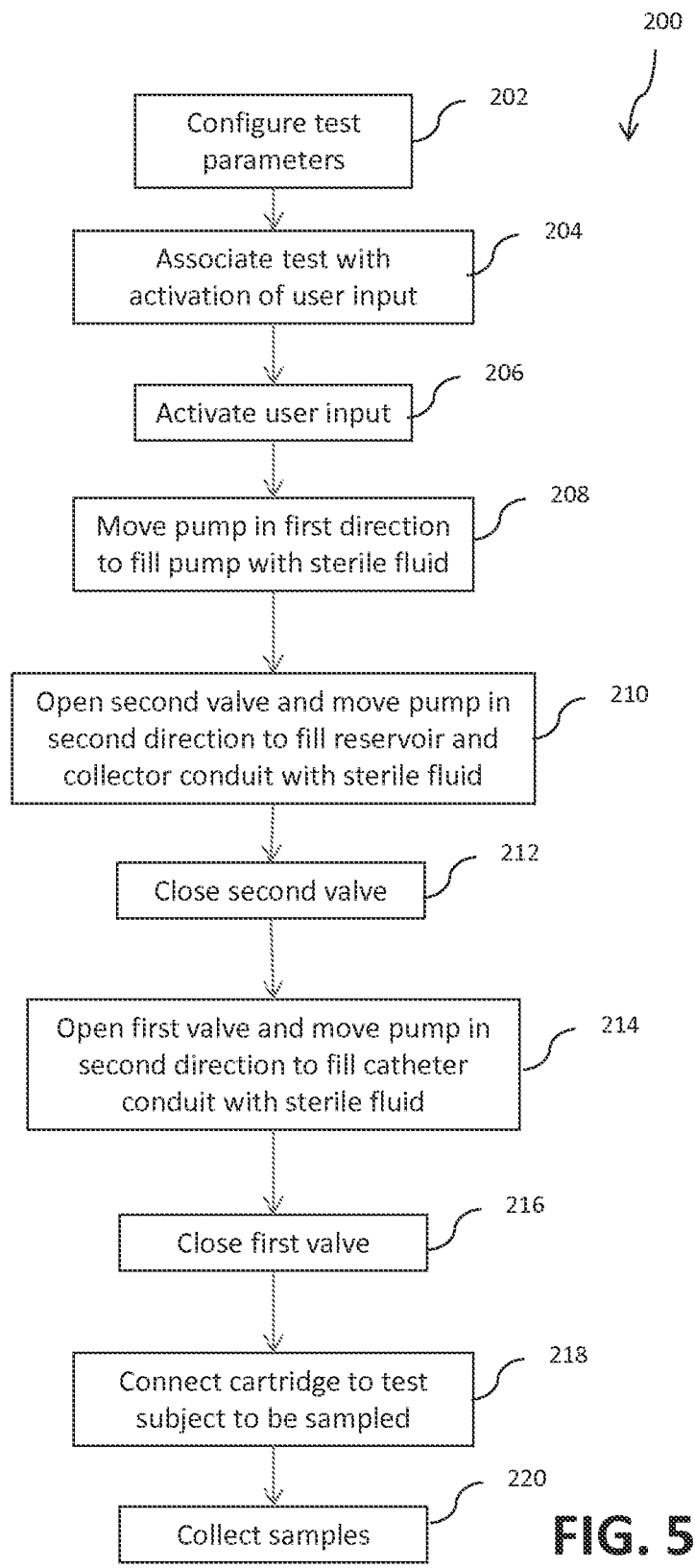
FIG. 5 illustrates an exemplary processing sequence for preparing an ABS apparatus and ABS cartridge for sampling.

FIG. 5 illustrates an exemplary processing sequence 200 for preparing an ABS apparatus 12 and ABS cartridge 10 for sampling. Although an exemplary sequence 200 is described for the exemplary ABS cartridge 10 and ABS apparatus 12 illustrated in FIG. 1, the sequence 200 may be used with other suitable ABS apparatus as well.

In block 202, the test parameters are configured. Exemplary parameters include the amount of fluid to be withdrawn, the frequency of sampling, and parameters associated with the sample collection area 98, such as associating particular sample collection vials or tubes with particular testing periods. Configuring the test parameters in block 202 may be performed at the ABS apparatus 12, or the test parameters can be configured remotely and uploaded or otherwise provided to ABS apparatus 12. The configured test parameters may be saved in memory 114 as a saved routine 118 (FIG. 3).

In block 204, the configured test parameters are associated with activation of user input, such as single button 110A. Associating the test parameters in block 204 may be performed at the ABS apparatus 12, or the association can be made remotely and uploaded or otherwise provided to ABS apparatus 12. The association may be saved in memory 114 as an instruction to start a routine, such as sequence 250 (see FIG. 4) when single button 110A is depressed or otherwise activated. In block 206, single button 110A is depressed or otherwise activated.

Prior to block 208, first valve 50 and second valve 52 are closed and third valve 54 is opened. In block 208, syringe pump 26 is moved in a first direction to fill syringe pump 26 with sterile fluid from the saline bag 96. Moving syringe pump 26 in a first or second direction may include moving plunger 30 directly or moving syringe mechanism 32 connected to plunger 30 through syringe mechanism connector 34.

Third valve 54 is then closed, and in block 210, second valve 52 is opened and pump 26 is moved in a second direction to fill reservoir 36 and collector conduit 42 with sterile fluid. In block 212, second valve 52 is closed. In block 214, first valve 50 is opened and pump 26 is moved in a second direction to fill catheter conduit 40 with sterile fluid. First valve 50 is closed in block 216. ABS cartridge 10 is then ready to be connected to the test subject to be sampled, as shown in block 218. If first connector 18 has not been connected to sample tubing, that step can be done at this point. Sample tubing is positioned to collect sample fluid from the test subject, and samples are collected in block 220. Block 220 may include at least a portion of exemplary sequence 250 (see FIG. 4).

FIG. 6 illustrates an exemplary processing sequence 250 for taking samples using an ABS apparatus 12 and ABS cartridge 10. Although an exemplary sequence 250 is described for the exemplary ABS cartridge 10 and ABS apparatus 12 illustrated in FIG. 1, the sequence 250 may be used with other suitable ABS apparatus as well.

In block 252, test parameters the test parameters are configured. In one embodiment, block 252 is similar to block 202 in sequence 200. Exemplary parameters include the amount of fluid to be withdrawn, the frequency of sampling, and parameters associated with the sample collection area 98, such as associating particular sample collection vials or tubes with particular testing periods. Configuring the test parameters in block 252 may be performed at the ABS apparatus 12, or the test parameters can be configured remotely and uploaded or otherwise provided to ABS apparatus 12. The configured test parameters may be saved in memory 114 as a saved routine 118 (FIG. 3). In block 254, the configured test parameters are associated with activation of user input, such as single button 110A. In one embodiment, block 254 is similar to block 204 in sequence 200. Associating the test parameters in block 204 may be performed at the ABS apparatus 12, or the association can be made remotely and uploaded or otherwise provided to ABS apparatus 12. The association may be saved in memory 114 as an instruction to start a routine, such as sequence 250 when single button 110A is depressed or otherwise activated.

In block 256, the test is activated. In one exemplary embodiment, the test is activated by depressing or otherwise activating single button 110A. In another exemplary embodiment, the test is activated remotely. In a more particular embodiment, a physician or other health care professional may review a current status of the patient and activate a test remotely, such as over a computer or other network, the internet, a smart phone, or other suitable mobile device. In still another exemplary embodiment, the test is activated automatically by a remote trigger, such as by a nurse at a centralized nursing station. In a more particular embodiment, a nurse may remotely activate the test prior to heading to the patient's location. In yet still another exemplary embodiment, the test is activated by a change in patient status. In a more particular embodiment, the one or more characteristics of the patient may be monitored, such as heart rate, temperature, or blood pressure. Suitable characteristics are typically monitored using head of bed technology common in intensive care units, critical care units, and emergency department rooms. In an illustrative embodiment, ABS apparatus 12 is operatively connected to one or more of the monitoring units, such that a change in one or more of the characteristics being monitored results in an activation of the test, and/or alerting one or more health care professionals as to the change in the patient's status.

In block 258, valves 54 and 52 are closed if open, and first valve 50 is opened. Pump 26 is moved in a first direction to draw sample fluid from the test subject being sampled through first connector 18, catheter conduit 40, first "T" connector 38, and into reservoir 36. First valve 50 is closed in block 260.

In block 262, second valve 52 is opened and pump 26 is moved in a second direction to force sample fluid from reservoir 36 through first T connector 38, through collector conduit 42 and second connector 20 into sample fraction collector 82. Second valve 52 is closed in block 264.

In block 266, first valve 50 is opened and pump 26 is moved in a second direction to force sterile fluid out of first connector 18 and flush catheter conduit 40. Block 266 may also return sample fluid to the subject through the sample tubing. First valve 50 is then closed in block 268.

In block 270, second valve 52 is opened and pump 26 is moved in a second direction to force sterile fluid out of the second connector 20 and flush collector conduit 42.

Second valve 52 is then closed in block 272.

In block 274, third valve 54 is opened and pump 26 is moved in a first direction to draw sterile fluid from saline bag 96 through third connector 22 and into pump 26 through syringe conduit 48. Third valve 54 may then be closed.

In block 276, ABS apparatus 12 checks to see if another sample is to be taken. If another sample is called for, the sequence returns to block 258. If no other sample is called for, the sequence ends in block 276. The decision in block 276 may be made by controller 80, external computer 86, or through user interface 92 based on the desired sampling parameters.

If, at any time in sequence 200 or sequence 250, there is insufficient fluid in syringe pump 26, pump 26 can be refilled by closing valves 50, 52, opening valve 54 and moving pump 26 in a first direction to draw fluid into barrel 28. Additionally, before or after this step, second valve 52 may be opened and pump 26 may be moved in a second direction to expel sample fluid from the reservoir 36, T connectors 38, 44 and conduit 42, 48. If at any time in sequence 200 or sequence 250, there is too much fluid in pump 26, thereby preventing syringe pump 26 from moving in a first direction because barrel 28 is already full, excess fluid can be purged by opening only second valve 52 and moving pump 26 in a second direction to expel sample fluid from pump 26.

Figure 7:
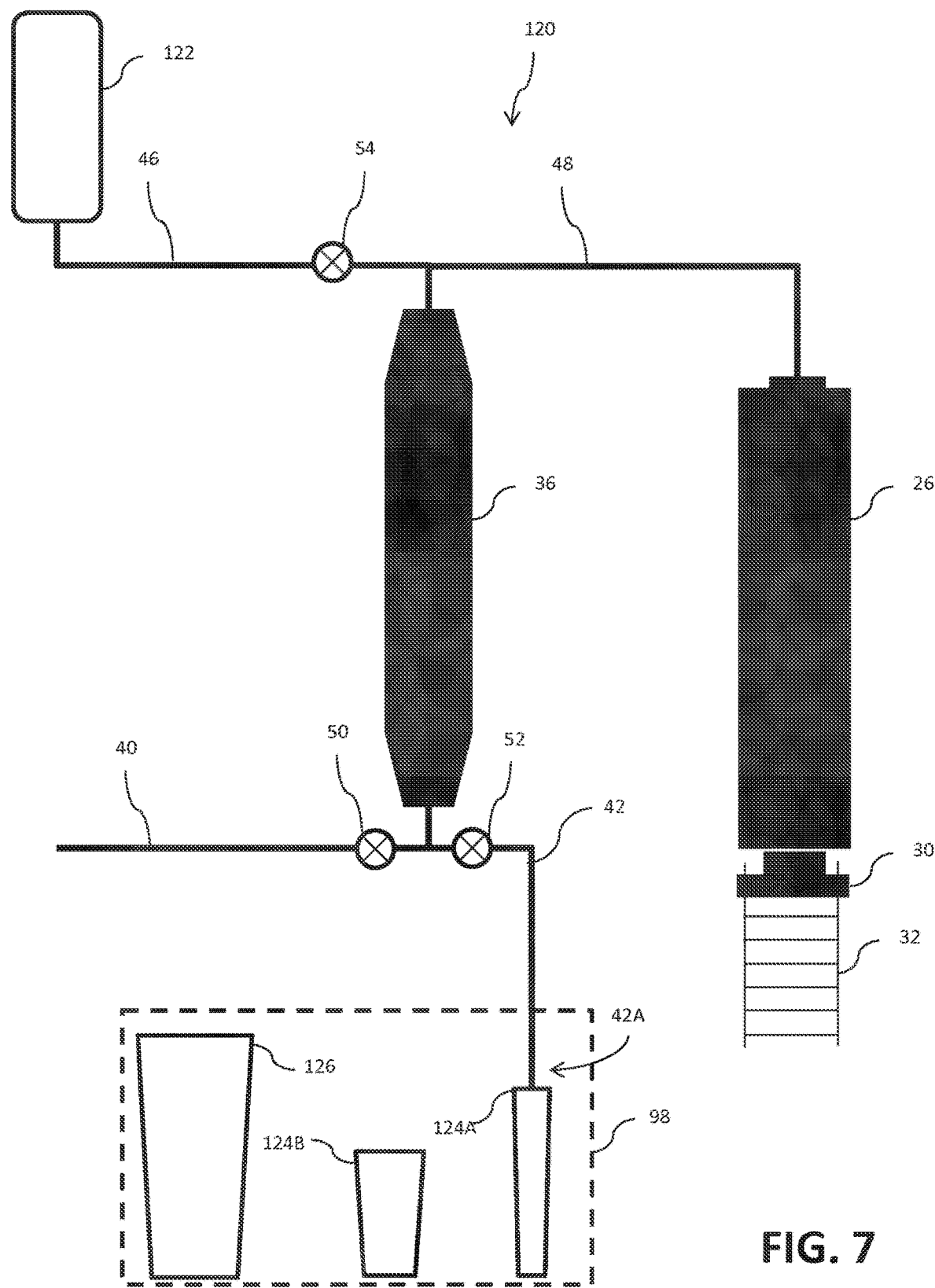
FIG. 7 illustrates an exemplary ABS apparatus for collecting multiple samples from a single fluid draw.

Referring next to FIG. 7, an additional ABS apparatus 120 is illustrated. ABS apparatus 120 is similar to ABS cartridge 10 and ABS apparatus 12, and ABS apparatus 88, and similar part numbers are used to illustrate similar parts. Reservoir conduit 46 of ABS apparatus 120 is fluidly connected to a solution 122, such as saline bag or other physiologically compatible solution, such as, but not limited to Ringer's solution. ABS apparatus 120 further includes a syringe pump 26 having plunger 30 operatively connected to a syringe mechanism 32. Syringe pump 26 is fluidly connected to fluid reservoir 36 by syringe conduit 48.

Fluid reservoir 36 is fluidly connected to solution 122 through reservoir conduit 46, flow through which is controlled by third valve 54. Fluid reservoir 36 is fluidly connected to a patient through catheter conduit 40, flow through which is controlled by first valve 50. Flow through collector conduit 42 is controlled by second valve 52. In one embodiment, valves 50, 52, 54 are operably connected to ABS apparatus 120 and controlled by controller 80 (FIG. 3).

Samples from reservoir 36 are provided through collector conduit 42 to sample collection area 98. In the illustrated embodiment, sample collection area 98 includes first sample vessel 124A and second sample vessel 124B. In the illustrated embodiment, first sample vessel 124A and second sample vessel 124B are different sizes. In other embodiments, first sample vessel 124A and second sample vessel 124B are the same size. Although sample vessels 124 are illustrated as first sample vessel 124A and 124B, in other embodiments, third, fourth, or additional sample vessels may also be included. Sample collection area 98 further includes waste fluid vessel 126. Sample collection area 98 can move at least one of an end 42A collector conduit 42, sample vessels 124, and waste fluid vessel 126 to selectively put reservoir 36 in fluid connection with one of sample vessels 124, and waste fluid vessel 126. In one embodiment, sample collection are 98 may include one or more sample selection valves (not shown) to place each sample vessel 124 and waste fluid vessel 126 into fluid communication with collector conduit 42.

In another embodiment, sample collection area 98 includes only a single sample vessel 124 at a time. In this embodiment, providing only a single sample vessel 124 reduces the necessary space and weight associated with sample collection area 98, which allows for a smaller and more compact ABS apparatus 12. In exemplary embodiments in which the sample vessel 124 is to be cooled after collection, such as refrigerated using Peltier cooling in sample collection area 98 as described above, providing only a single sample vessel 124 to be cooled reduces the power requirements of ABS apparatus 12. Following removal of the filled sample vessel 124 from sample collection area 98, a replacement sample vessel 124 is positioned in sample collection area for collection of a subsequent sample. In one embodiment, a plurality of empty sample vessels 124 are queued as a magazine (not shown) to positioned in sample collection area 98 following removal of the filled sample vessel 124. In a more particular embodiment, sample collection area may automatically position the next empty sample vessel 124 from the magazine in the sample collection area following removal of the filled sample vessel 124.

In illustrative embodiments where ABS apparatus 12, ABS apparatus 88, and/or ABS apparatus 120 is provided as a portable embodiment, as described above, the reduction in space, weight, and power requirements allow for a more compact design. The use of a portable ABS allows for greater mobility of the patient during sample collection. Patients may be able to go about daily activities, such as eating meals, sending emails, reading a book, and walking to a restroom, while attached to an ABS unit. Greater mobility and fewer sticks may lead to reduced stress.

FIG. 8 illustrates an exemplary processing sequence 300 for preparing an ABS apparatus 120 for sampling. Although an exemplary sequence 300 is described for the exemplary ABS apparatus 120 illustrated in FIG. 7, the sequence 300 may be used with other suitable ABS apparatus as well.

In block 302, the sample collection area 98 is set up. First sample collection vessel 124A and second sample collection vessel 124B are positioned in the sample collection area 98, along with waste fluid vessel 126. First valve 50 and second valve 52 are closed and third valve 54 is opened. In block 304, syringe pump 26 is moved in a first direction to fill syringe pump 26 with sterile fluid from the saline bag 96. Moving syringe pump 26 in a first or second direction may include moving plunger 30 directly or moving syringe mechanism 32 connected to plunger 30 through syringe mechanism connector 34.

Third valve 54 is then closed, and in block 306, second valve 52 is opened and pump 26 is moved in a second direction to fill reservoir 36 and collector conduit 42 with sterile fluid. In block 308, second valve 52 is closed. In block 310, first valve 50 is opened and pump 26 is moved in a second direction to fill catheter conduit 40 with sterile fluid. First valve 50 is closed in block 312. ABS apparatus 120 is then ready to be connected to the test subject to be sampled, as shown in block 314. If first connector 18 has not been connected to sample tubing, that step can be done at this point. Sample tubing is positioned to collect sample fluid from the test subject, and samples are collected in block 316. Block 316 may include at least a portion of exemplary sequence 350 or sequence 400 (see FIGS. 9A and 9B).

Figure 9A:
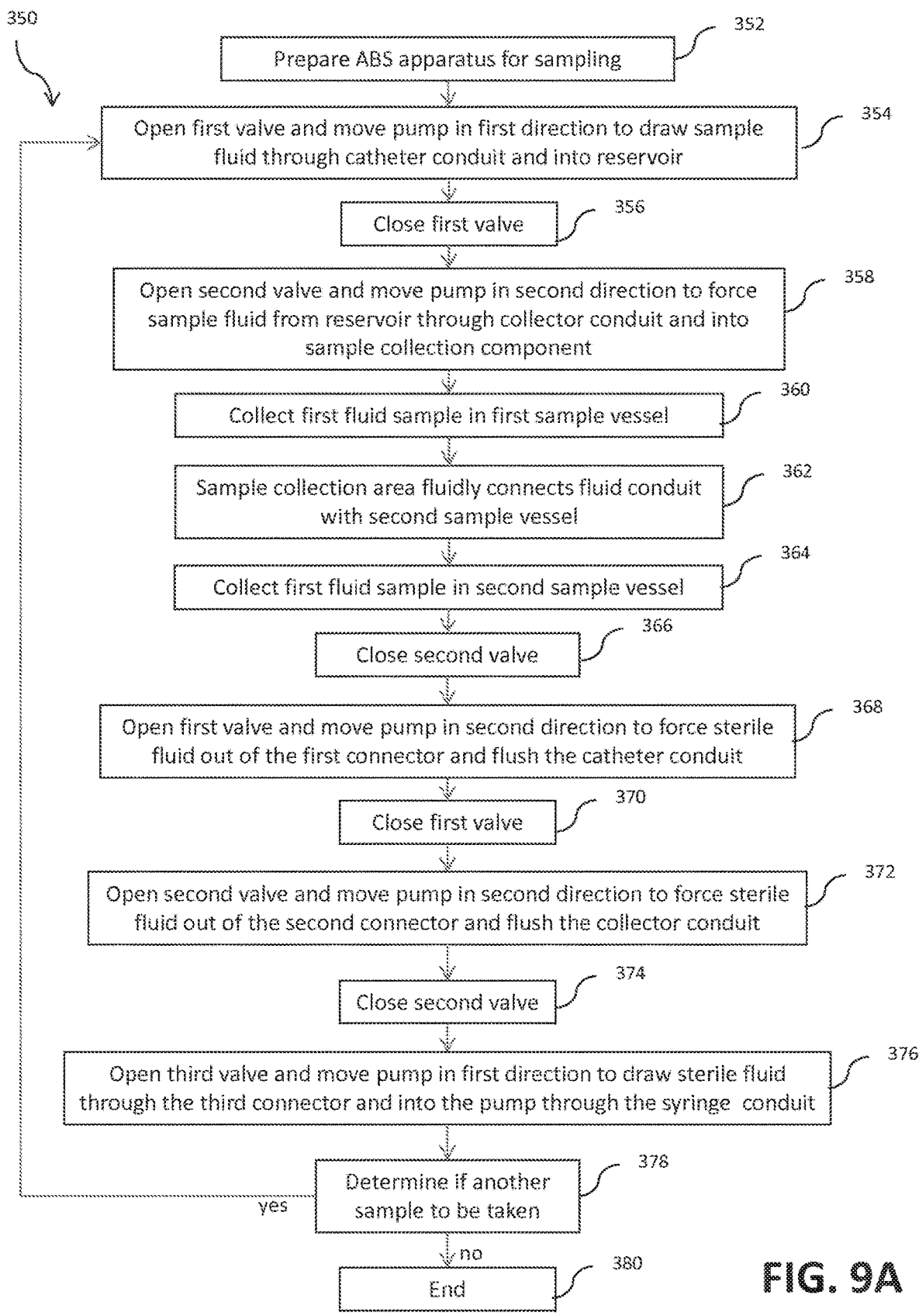
FIG. 9A illustrates an exemplary processing sequence for taking samples using the ABS apparatus of FIG. 7.

FIG. 9A illustrates an exemplary processing sequence 350 for preparing an ABS apparatus 120 for sampling. Although an exemplary sequence 350 is described for the exemplary ABS apparatus 120 illustrated in FIG. 7, the sequence 350 may be used with other suitable ABS apparatus as well.

In block 352, the ABS apparatus 120 is prepared for sampling. Block 352 may include sequence 350 of FIG. 8. In block 354, valves 54 and 52 are closed if open, and first valve 50 is opened. Pump 26 is moved in a first direction to draw sample fluid from the test subject being sampled through first connector 18, catheter conduit 40, and into reservoir 36. First valve 50 is closed in block 356.

In block 358, second valve 52 is opened and pump 26 is moved in a second direction to force sample fluid from reservoir 36 through collector conduit 42 into first sample vessel 124A. Sample collection area 98 collects a predetermined amount of a first fluid sample in first sample vessel 124A in block 360. Pump 26 then stop.

Sample collection area 98 then fluidly disconnects from the first sample vessel 124A and fluid connects to second sample vessel 124B in block 362. In one exemplary embodiment, block 362 is performed by moving end 42A of collector conduit 42 from a position proximal to first sample vessel 124A to a position proximal to second sample vessel 124B. In another exemplary embodiment, block 362 is performed by moving first sample vessel 124A from a position proximal to an end 42A of collector conduit 42 to another position, and moving second sample vessel 124B from another position to a position proximal to the end 42A of collector conduit. In yet another exemplary embodiment, block 362 is performed by closing a first collector valve (not shown) controlling fluid communication between reservoir 36 and first sample vessel 124A and opening a second collector valve (not shown) controlling fluid communication between reservoir 36 and second sample vessel 124B.

In block 364, pump 26 is again moved in the second direction to force sample fluid from reservoir 36 through collector conduit 42 into second sample vessel 124B. Sample collection area 98 collects a predetermined amount of a second fluid sample in second sample vessel 124B in block 364. Pump 26 then stop.

In block 366, the second valve is closed. In block 368, first valve 50 is opened and pump 26 is moved in a second direction to force sterile fluid out of first connector 18 and flush catheter conduit 40. Block 368 may also return sample fluid to the subject through the sample tubing. First valve 50 is then closed in block 370.

In block 372, second valve 52 is opened and pump 26 is moved in a second direction to force sterile fluid out of the second connector 20 and flush collector conduit 42. Second valve 52 is then closed in block 374.

In block 376, third valve 54 is opened and pump 26 is moved in a first direction to draw sterile fluid from saline bag 96 through third connector 22 and into pump 26 through syringe conduit 48. Third valve 54 may then be closed.

In block 378, ABS apparatus 120 checks to see if another sample is to be taken. If another sample is called for, the sequence returns to block 354. If no other sample is called for, the sequence ends in block 380. The decision in block 378 be made by controller 80, external computer 86, or through user interface 92 based on the desired sampling parameters.

Sequence 350 avoids a full recycling of the device to obtain additional samples using different anticoagulants or different isotopically labeled internal standards for mass spectrometry. Additional sample can be purged from reservoir 36 and/or collector conduit 42 by fluidly connecting waste fluid vessel 126 to reservoir 36 and opening second valve 52 while moving pump 26 in the second direction.

If, at any time in sequence 300 (FIG. 8), sequence 350 (FIG. 9A), sequence 400 (FIG. 9B), there is insufficient fluid in syringe pump 26, pump 26 can be refilled by closing valves 50, 52, opening valve 54 and moving pump 26 in a first direction to draw fluid into barrel 28. Additionally, before or after this step, second valve 52 may be opened and pump 26 may be moved in a second direction to expel sample fluid from the reservoir 36, T connectors 38, 44 and conduit 42, 48. If at any time in sequence 200 or sequence 250, there is too much fluid in pump 26, thereby preventing syringe pump 26 from moving in a first direction because barrel 28 is already full, excess fluid can be purged by opening only second valve 52 and moving pump 26 in a second direction to expel sample fluid from pump 26.

Figure 9B:
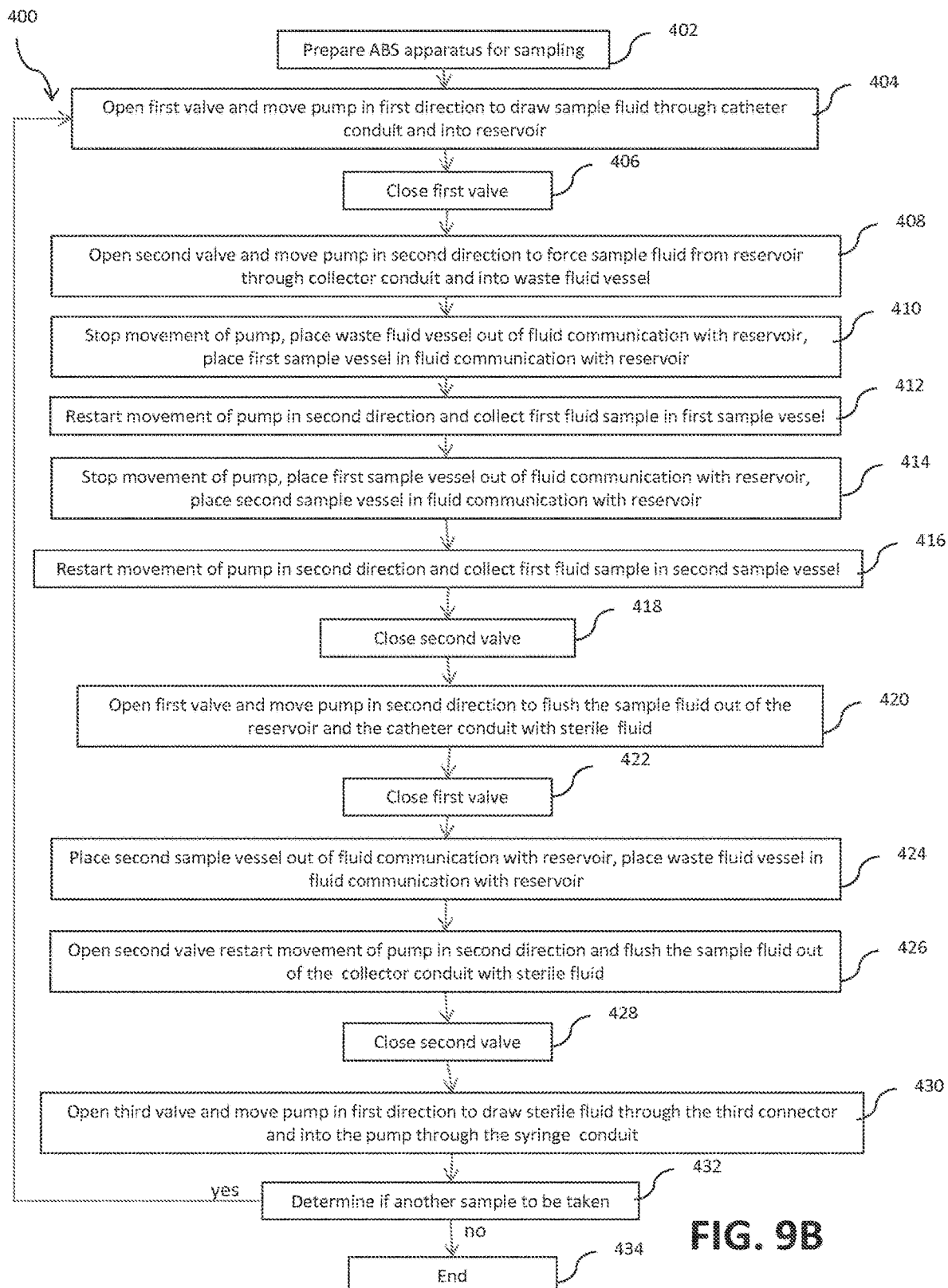
FIG. 9B illustrates another exemplary processing sequence for taking samples using the ABS apparatus of FIG. 7.

FIG. 9B illustrates another exemplary processing sequence 400 for preparing an ABS apparatus 120. Although an exemplary sequence 400 is described for the exemplary ABS apparatus 120 illustrated in FIG. 7, the sequence 400 may be used with other suitable ABS apparatus as well.

In block 402, the ABS apparatus 120 is prepared for sampling. Block 402 may include sequence 350 of FIG. 8. In block 404, valves 54 and 52 are closed if open, and first valve 50 is opened. Pump 26 is moved in a first direction to draw sample fluid from the test subject being sampled through first connector 18, catheter conduit 40, and into reservoir 36. First valve 50 is closed in block 406.

In block 408, second valve 52 is opened and pump 26 is moved in a second direction to force a portion of the sample fluid from reservoir 36 through collector conduit 42 into waste fluid vessel 126. In step 410, movement of pump 26 is stopped, and sample collection area 98 fluidly disconnects waste fluid vessel 126 from the reservoir 36 and fluidly connects reservoir 36 to first sample vessel 124A. In one exemplary embodiment, block 410 is performed by moving end 42A of collector conduit 42 from a position proximal to waste fluid vessel 126 to the first sample vessel 124A. In another exemplary embodiment, block 410 is performed by moving waste fluid vessel 126 from a position proximal to an end 42A of collector conduit to another position, and moving first sample vessel 124A from another position to a position proximal to end 42A of collector conduit 42. In yet another exemplary embodiment, block 410 is performed by closing a first collector valve (not shown) controlling fluid communication between reservoir 36 and waste fluid vessel 126 and opening a second collector valve (not shown) controlling fluid communication between reservoir 36 and first sample vessel 124A.

In block 412, movement of pump 26 is restarted in the second direction to force sample fluid from reservoir 36 through collector conduit 42 into first sample vessel 124A. A predetermined amount of sample is collected in first sample vessel 124A by moving plunger 30 of pump 26 a predetermined distance. In block 414, movement of pump 26 is stopped, and sample collection area 98 fluidly disconnects first sample vessel 124A from the reservoir 36 and fluidly connects reservoir 36 to second sample vessel 124B. In one exemplary embodiment, block 414 is performed by moving end 42A of collector conduit 42 from a position proximal to first sample vessel 124A to the second sample vessel 124B. In another exemplary embodiment, block 414 is performed by moving first sample vessel 124A from a position proximal to an end 42A of collector conduit to another position, and moving second sample vessel 124B from another position to a position proximal to end 42A of collector conduit 42. In yet another exemplary embodiment, block 414 is performed by closing a second collector valve (not shown) controlling fluid communication between reservoir 36 and first sample vessel 124A and opening a third collector valve (not shown) controlling fluid communication between reservoir 36 and second sample vessel 124B.

In block 416, movement of pump 26 is restarted in the second direction to force sample fluid from reservoir 36 through collector conduit 42 into second sample vessel 124B. A predetermined amount of sample is collected in second sample vessel 124B by moving plunger 30 of pump 26 a predetermined distance. In block 418, second valve is then closed. In block 420, first valve 50 is opened and pump 26 is moved in a second direction to flush reservoir 36 and catheter conduit 40 with sterile fluid. Block 420 may return sample fluid to the subject through the sample tubing. First valve 50 is then closed in block 422.

In block 424, movement of pump 26 is stopped, and sample collection area 98 fluidly disconnects second sample vessel 124B from the reservoir 36 and fluidly connects reservoir 36 to waste fluid vessel 126. In one exemplary embodiment, block 424 is performed by moving end 42A of collector conduit 42 from a position proximal to second sample vessel 124B to the waste fluid vessel 126. In another exemplary embodiment, block 424 is performed by moving second sample vessel 124B from a position proximal to an end 42A of collector conduit to another position, and moving waste fluid vessel 126 from another position to a position proximal to end 42A of collector conduit 42. In yet another exemplary embodiment, block 424 is performed by closing a third collector valve (not shown) controlling fluid communication between reservoir 36 and second sample vessel 124B and opening a first collector valve (not shown) controlling fluid communication between reservoir 36 and waste fluid vessel 126.

In block 426, second valve 52 is opened and pump 26 is moved in the second direction to flush collection conduit 42 with sterile fluid. The flushed fluid is deposited in waste fluid vessel 126, where it may be disposed of Second valve 52 is then closed in block 428.

If additional sterile fluid is needed in the system, in block 430, third valve 54 is opened and pump 26 is moved in the first direction to draw sterile fluid from saline bag 96 through third connector 22 and into pump 26 through syringe conduit 48. Third valve 54 may then be closed.

In block 432, ABS apparatus 120 checks to see if another sample is to be taken. If another sample is called for, the sequence returns to block 404. If no other sample is called for, the sequence ends in block 434. The decision in block 432 be made by controller 80, external computer 86, or through user interface 92 based on the desired sampling parameters.

Additional sample can be purged from reservoir 36 and/or collector conduit 42 by fluidly connecting waste fluid vessel 126 to reservoir 36 and opening second valve 52 while moving pump 26 in the second direction.

The frequency and volumes of samples taken from the test subject depend on the needs of the test and decisions of medical personnel. In one exemplary embodiment, samples are collected from the test subject at a regular frequency of about every 60 seconds to every several hours. In another exemplary embodiment, samples are collected at predetermined times, a predetermined regular frequency, a variable time, or some combination stored in memory or programmed by the controller. In yet another exemplary embodiment, a sample will be collected upon a signal from ABS apparatus 12. In one exemplary embodiment, sample volumes of about 25 µL to about 4 mL are collected. In another exemplary embodiment, sample volumes of about 5 µL to about 4 mL are collected. In still another exemplary embodiment, sample volumes of less than about 5 µL are collected. In yet still another exemplary embodiment, sample volumes of about 4 mL to about 10 mL or more are collected. Other frequencies and volumes than those presented may also be used. In one exemplary embodiment, a log file identifying at least one of the patient, sample, caregiver, and time taken are recorded by ABS apparatus 120 in memory 114. In another exemplary embodiment, frequency and volume are selected from several options presented on user interface 92. In still another exemplary embodiment, a saved routine 118 including frequency and volume settings stored in memory 114 is selected from several options presented on user interface 92.

Figure 10:
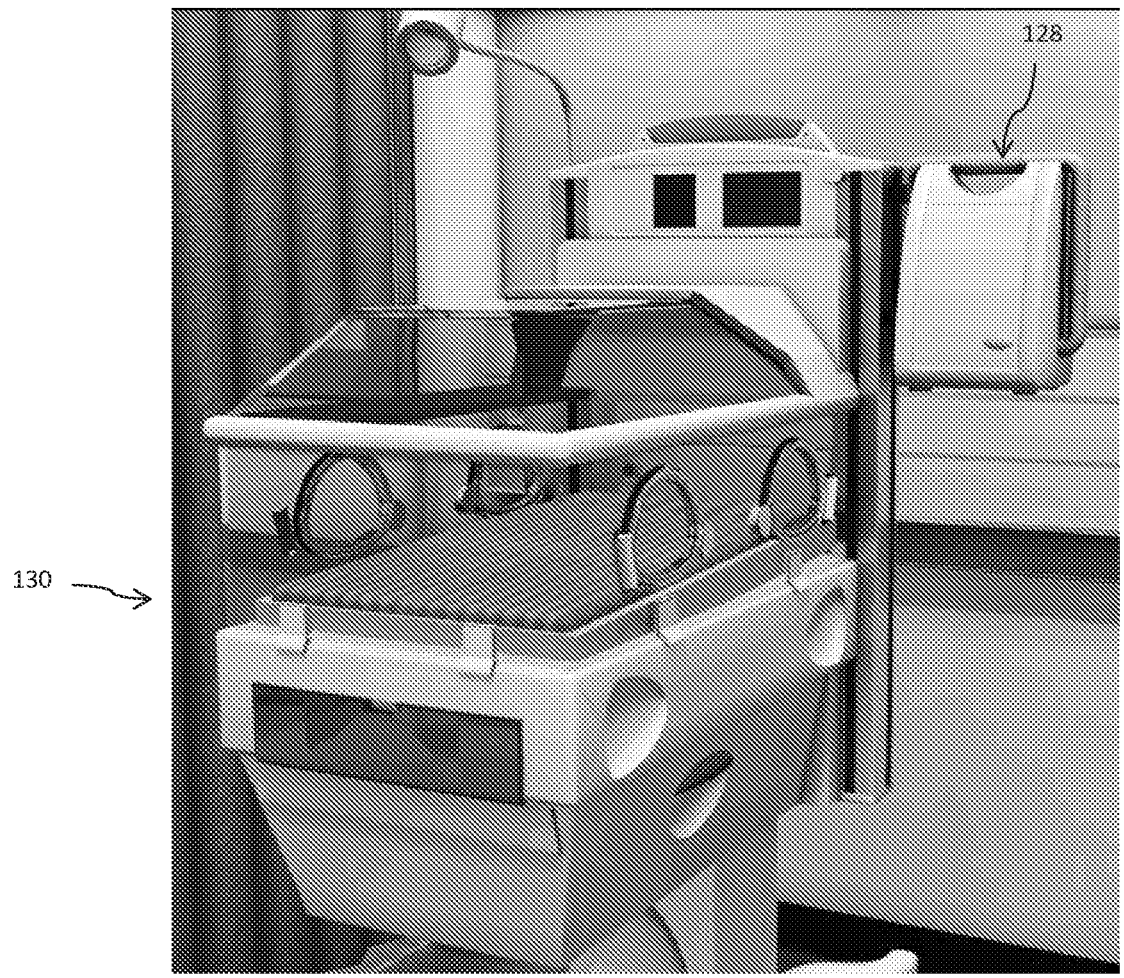
FIG. 10 shows an illustrative ABS apparatus attached to a neonate isolette.

Referring next to FIG. 10, an exemplary ABS apparatus 128 is illustrated attached to a neonatal isolette 130. ABS apparatus 128 may be similar to ABS apparatus 12, ABS apparatus 88, and/or ABS apparatus 120, and similar part numbers are used to illustrate similar parts.

Figure 11A:
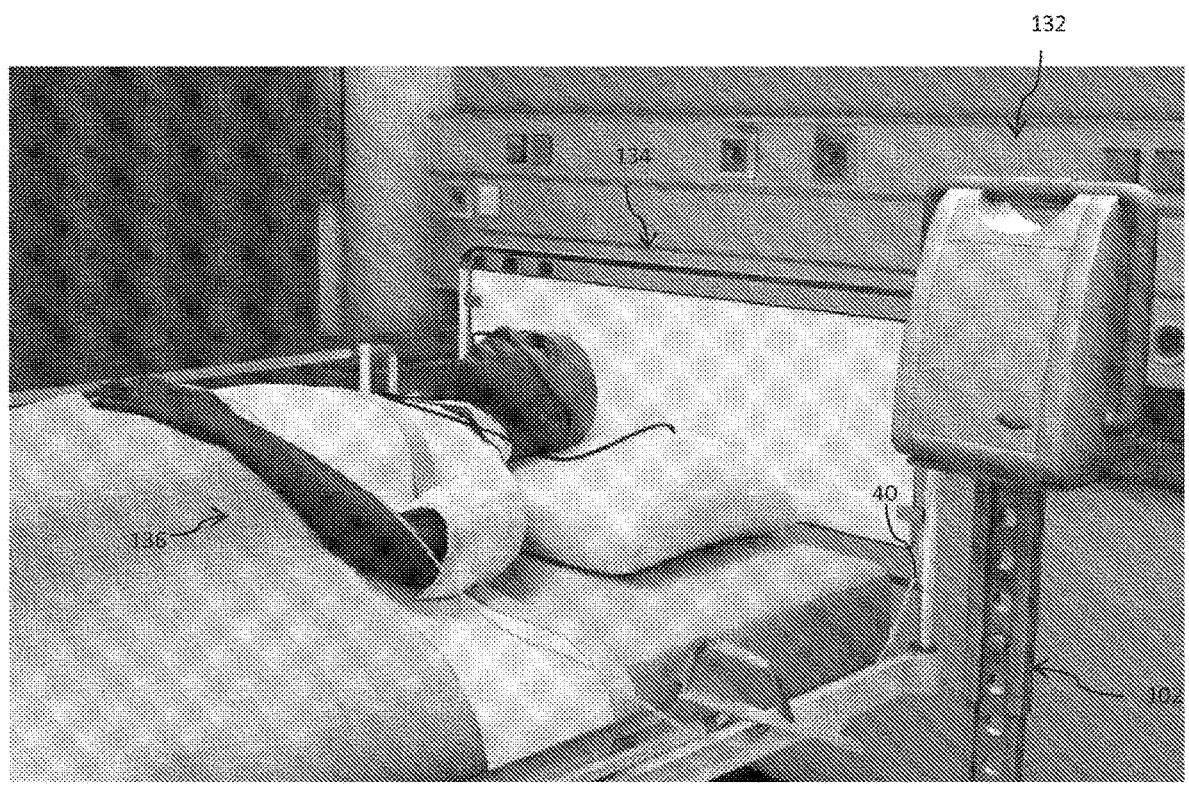
FIGS. 11A and 11B shows an illustrative ABS apparatus attached to a patient in a health-care setting.
Figure 11B:
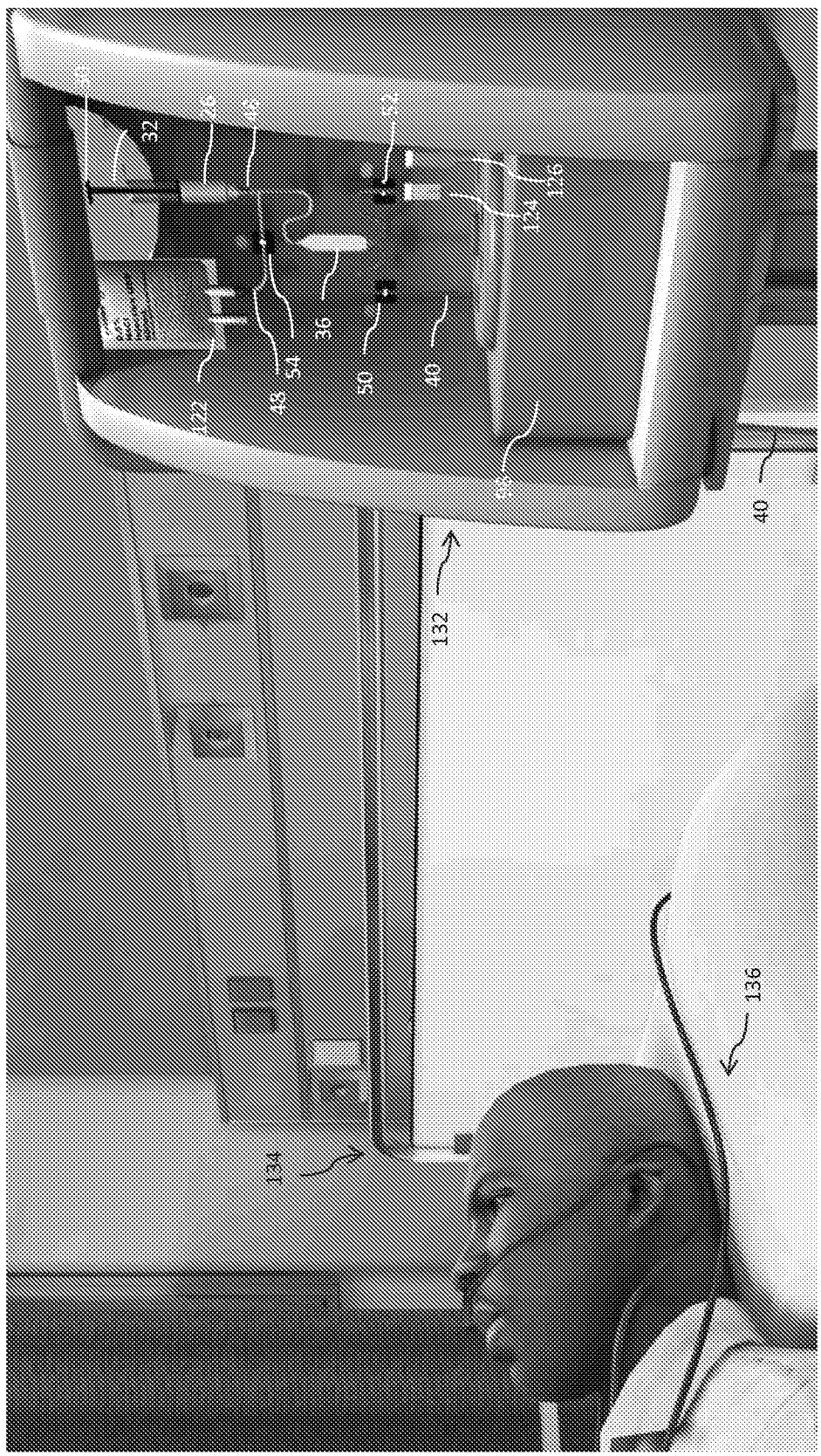

Referring next to FIGS. 11A and 11B, another exemplary ABS apparatus 132 is illustrated in a health care setting. ABS apparatus 132 may be similar to ABS apparatus 12, ABS apparatus 88, ABS apparatus 120, and/or ABS apparatus 132, and similar part numbers are used to illustrate similar parts. ABS apparatus 132 illustratively includes a stationary or wheeled stand 102 for positioning ABS apparatus 132 near a head of patient bed 134. As illustrated in FIG. 11B, reservoir conduit 46 of ABS apparatus 120 is fluidly connected to a solution 122, such as saline bag. ABS apparatus 132 further includes a syringe pump 26 having plunger 30 operatively connected to a syringe mechanism 32. Syringe pump 26 is fluidly connected to fluid reservoir 36 by syringe conduit 48. Fluid reservoir 36 is fluidly connected to solution 122 through reservoir conduit 46, flow through which is controlled by third valve 54. Fluid reservoir 36 is fluidly connected to a patient 136 through catheter conduit 40, flow through which is controlled by first valve 50. Flow through collector conduit 42 is controlled by second valve 52. In one embodiment, valves 50, 52, 54 are operably connected to ABS apparatus 120 and controlled by controller 80. Samples from reservoir 36 are provided through collector conduit 42 to sample collection area 98. In the illustrated embodiment, sample collection area 98 includes a sample vessel 124 and waste fluid vessel 126.

Figure 12:
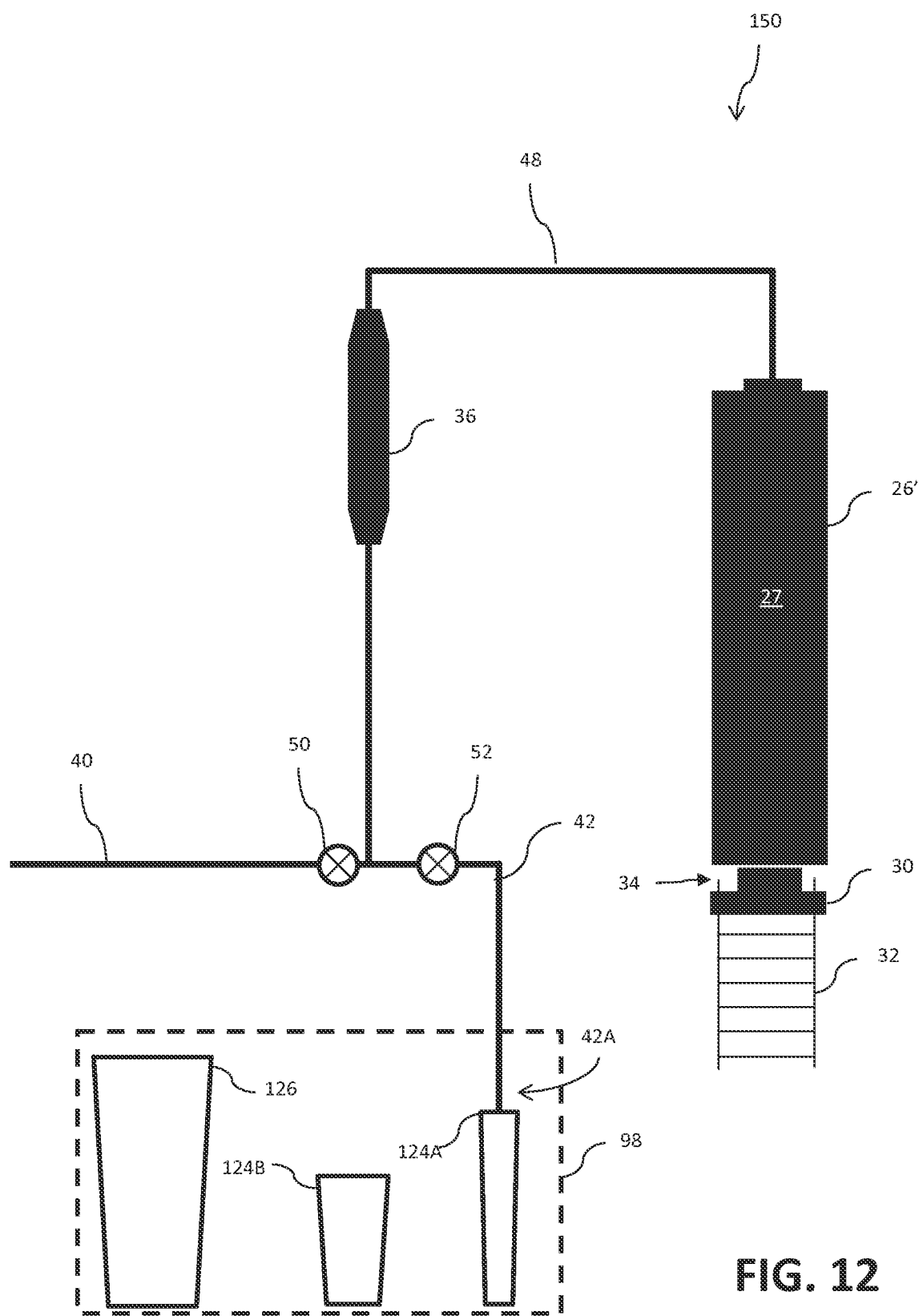
FIG. 12 illustrates another exemplary ABS apparatus for collecting multiple samples from a single fluid draw.

Referring next to FIG. 12, in another embodiment, an additional ABS apparatus 150 is illustrated. ABS apparatus 150 is similar to ABS cartridge 10, ABS apparatus 12, ABS apparatus 88, and ABS apparatus 120, and similar part numbers are used to illustrate similar parts. ABS apparatus 150 includes a pump 26' having plunger 30 operatively connected to a mechanism 32. Pump 26' is fluidly connected to fluid reservoir 36 by conduit 48. In one exemplary embodiment, a volume of fluid reservoir 36 is relatively small compared to the amount of fluid provided in an interior 27 of pump 26'.

In one exemplary embodiment, an interior 27 of pump 26' is prefilled with a sterile saline or other physiologically compatible solution, such as, but not limited to Ringer's solution. In one exemplary embodiment, pump 26' is a pre-filled sterile cartridge isolated from one or more of the remaining structure. In one exemplary embodiment, pump 26' is a syringe pump including a plunger 30 or other external structure. As shown in FIG. 12, pump 26' is illustratively connected to mechanism 32. A mechanism connector 34 connects mechanism 32 to plunger 30 such that movement of mechanism 32 in one direction moves plunger 30 in a first direction, and movement of mechanism 32 is another direction moves plunger 30 in a second direction.

Fluid reservoir 36 is fluidly connected to a patient through catheter conduit 40, flow through which is controlled by first valve 50. Flow through collector conduit 42 is controlled by second valve 52. In one embodiment, valves 50 and 52 are operably connected to ABS apparatus 150 and controlled by controller 80 (FIG. 3). Samples from reservoir 36 are provided through collector conduit 42 to sample collection area 98. In one exemplary embodiments, the samples collected by ABS apparatus 150 have volumes of as little as 0.01 cm$^3$, 0.05 cm$^3$, as great as 0.1 cm$^3$, 0.2 cm$^3$, or within any range defined between any two of these values, such as 0.01 cm$^3$ to 0.2 cm$^3$ or 0.05 cm$^3$ to 0.1 cm$^3$.

Figure 13:
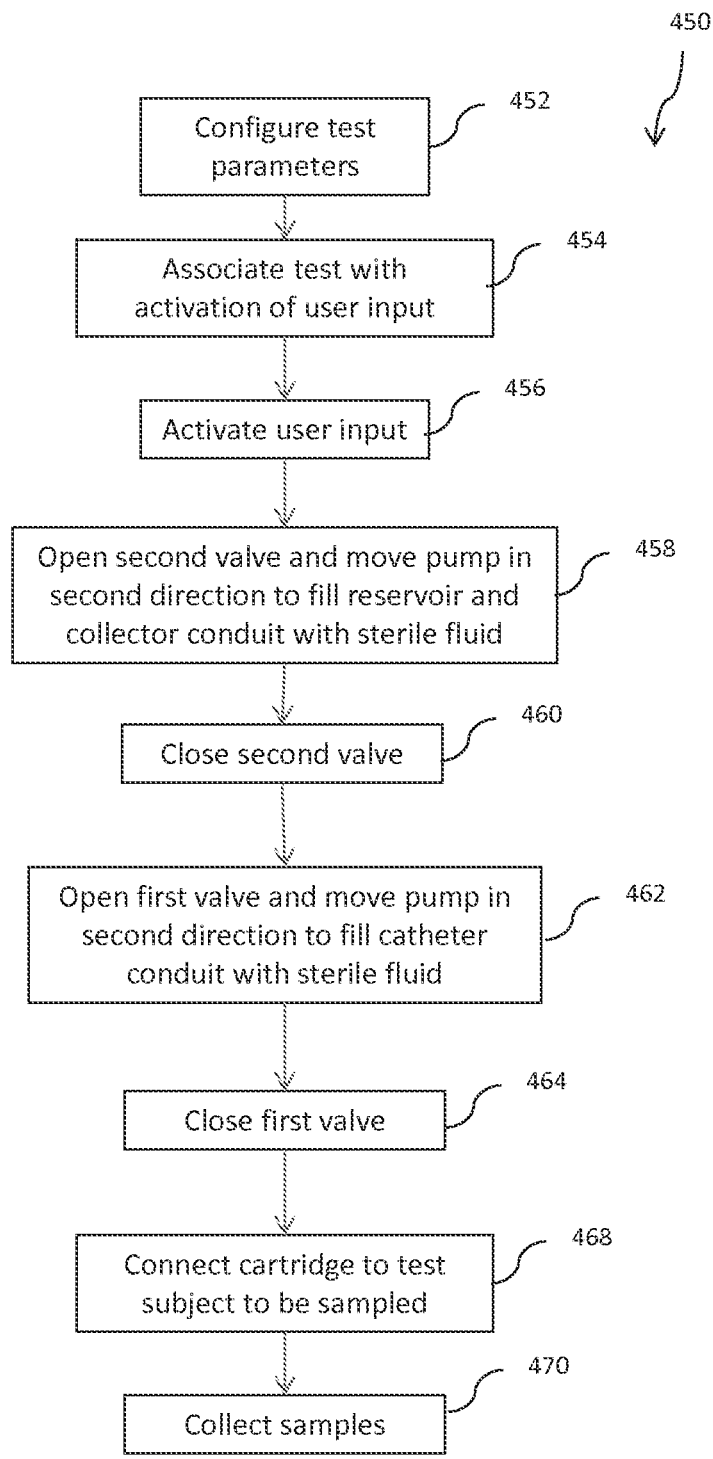
FIG. 13 illustrates an exemplary processing sequence for preparing the ABS apparatus of FIG. 12 for sampling.

FIG. 13 illustrates an exemplary processing sequence 450 for preparing an ABS apparatus 150 for sampling. Although an exemplary sequence 450 is described for the exemplary ABS apparatus 150 illustrated in FIG. 12, the sequence 450 may be used with other suitable ABS apparatus as well.

In block 452, the test parameters are configured. Exemplary parameters include the amount of fluid to be withdrawn, the frequency of sampling, and parameters associated with the sample collection area 98, such as associating particular sample collection vials or tubes with particular testing periods. Configuring the test parameters in block 452 may be performed at the ABS apparatus 150, or the test parameters can be configured remotely and uploaded or otherwise provided to ABS apparatus 150. The configured test parameters may be saved in memory 114 as a saved routine 118 (FIG. 3).

In block 454, the configured test parameters are associated with activation of a user input, such as single button 110A. Associating the test parameters in block 454 may be performed at the ABS apparatus 150, or the association can be made remotely and uploaded or otherwise provided to ABS apparatus 150. The association may be saved in memory 114 as an instruction to start a routine, such as routine 500 (see FIG. 14) when a user input such as single button 110A is depressed or otherwise activated. In block 456, a user input such as single button 110A is depressed or otherwise activated.

Prior to block 458, first valve 50 and second valve 52 are closed. In block 458, second valve 52 is opened and pump 26' is moved in a second direction to fill reservoir 36 and collector conduit 42 with sterile fluid provided from interior 27 of pump 26'. In block 460, second valve 52 is closed. In block 462, first valve 50 is opened and pump 26' is moved in a second direction to fill catheter conduit 40 with sterile fluid. First valve 50 is closed in block 464. ABS apparatus 150 is then ready to be connected to the test subject to be sampled, as shown in block 468. If first connector 18 has not been connected to sample tubing, that step can be done at this point. Sample tubing is positioned to collect sample fluid from the test subject, and samples are collected in block 470. Block 470 may include at least a portion of exemplary sequence 500 (see FIG. 14).

Figure 14:
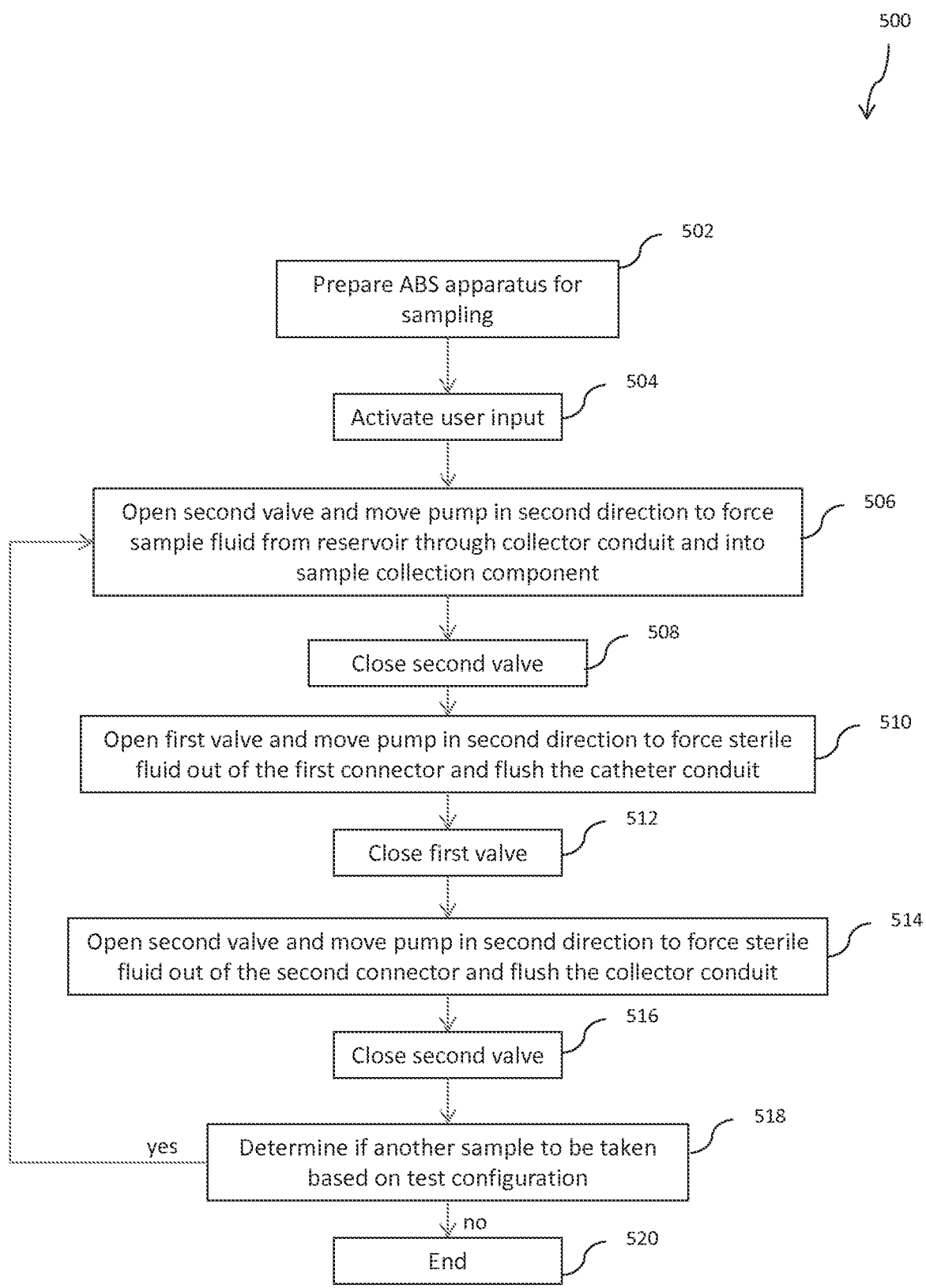
FIG. 14 illustrates an exemplary processing sequence for taking samples using the ABS apparatus of FIG. 12.

FIG. 14 illustrates an exemplary processing sequence 500 for preparing an ABS apparatus 150 for sampling. Although an exemplary sequence 500 is described for the exemplary ABS apparatus 150 illustrated in FIG. 12, the sequence 500 may be used with other suitable ABS apparatus as well.

In block 502, the ABS apparatus 150 is prepared for sampling. Block 502 may include sequence 450 of FIG. 13. In block 504, the test is activated. In one exemplary embodiment, the test is activated by depressing or otherwise activating a user input such as single button 110A. In another exemplary embodiment, the test is activated remotely. In a more particular embodiment, a physician or other health care professional may review a current status of the patient and activate a test remotely, such as over a computer or other network, the internet, a smart phone, or other suitable mobile device. In still another exemplary embodiment, the test is activated automatically by a remote trigger, such as by a nurse at a centralized nursing station. In a more particular embodiment, a nurse may remotely activate the test prior to heading to the patient's location. In yet still another exemplary embodiment, the test is activated by a change in patient status. In a more particular embodiment, the one or more characteristics of the patient may be monitored, such as heart rate, temperature, or blood pressure.

In block 506 second valve 52 is opened and pump 26' is moved in a second direction to force sample fluid from reservoir 36 through first T connector 38, through collector conduit 42 and second connector 20 into sample fraction collector 82. Second valve 52 is closed in block 508.

In block 510, first valve 50 is opened and pump 26' is moved in a second direction to force sterile fluid out of first connector 18 and flush catheter conduit 40. Block 510 may also return sample fluid to the subject through the sample tubing. First valve 50 is then closed in block 512.

In block 514, second valve 52 is opened and pump 26' is moved in a second direction to force sterile fluid out of the second connector 20 and flush collector conduit 42.

Second valve 52 is then closed in block 516.

In block 518, ABS apparatus 150 determines if another sample is to be taken. If another sample is called for, the sequence 500 returns to block 506. If no other sample is called for, the sequence 500 ends in block 520. The decision in block 518 may be made by controller 80, external computer 86, or through user interface 92 based on the desired sampling parameters.

The features of the disclosure disclosed in the above description, the claims and the figures can be of importance individually as well as in any combination for the realization of the disclosure in its various embodiments.

What is claimed is:

1. A method of collecting a fluid sample from a test subject with an automated fluid sampling device, the method comprising:
    connecting the test subject to the automated fluid sampling device, the fluid sampling device including:
        a pump being moveable in a first direction to draw fluid into the pump and a second direction to expel fluid from the pump;
        a reservoir in fluid communication with the pump, the reservoir having a first opening and a second opening;
        a first conduit fluidly connecting the reservoir to a first fluid fitting configured to fluidly connect the reservoir to tubing having a distal end inserted into the test subject;
        a second conduit fluidly connecting the reservoir to a second fluid fitting configured to connect the reservoir to a sample collection component;
        a third conduit fluidly connecting the reservoir to a third fluid fitting configured to connect the reservoir to a sterile fluid supply; and
        a single input component defined by a single button configured to activate a predetermined routine on the automated fluid sampling device when the single button is activated to reduce operation errors of a user of the automated fluid sampling device;
    wherein the pump is configured to move in the first direction and second direction in response to movement of a portion of the fluid sampling device and the conduits are configured such that a first valve of the fluid sampling device controls fluid flow in the first conduit, a second valve of the fluid sampling device controls fluid flow in the second conduit, and a third valve of the fluid sampling device controls fluid flow in the third conduit, each valve having an open state and a closed state; and wherein the fluid sampling device includes a controller for controlling the pump and valve;
    wherein the pump, the reservoir, the first fluid conduit, the second fluid conduit, and the third fluid conduit are secured to a frame by support components formed as part of the frame and configured to be removably attached to the first valve, the second valve, and the third valve of the fluid sampling device;
    activating the predetermined routine on the automated fluid sampling device by activating the single button on the automated fluid sampling device, said predetermined routine including the steps of:
        opening the first valve, and moving the pump in the first direction to draw sample fluid through the first conduit and into the reservoir; thereby forming a sample fluid/sterile fluid interface;
        opening the second valve, and moving the pump in the second direction to force a sample fluid from the reservoir through the second conduit to the sample collection component, the sample collection component collecting a predetermined amount of fluid;
        re-opening the first valve, and moving the pump in the second direction to force the sterile fluid out of the first fluid fitting, thereby flushing the first conduit;
        re-opening the second valve, and moving the pump in the second direction to force the sterile fluid out of the second fluid fitting, thereby flushing the second conduit and the sample collection component, and
        opening the third valve, and moving the pump in the first direction to draw the sterile fluid through the third fluid fitting and into the pump through the first opening of the third conduit.

2. The method of claim 1, wherein the automated fluid sampling device further includes non-volatile memory, wherein the predetermined routine is saved in the non-volatile memory.

3. The method of claim 2, wherein the predetermined routine includes the predetermined amount of fluid collected in the sample collection component.

4. The method of claim 3, wherein the predetermined routine is repeated.

5. The method of claim 4, wherein the non-volatile memory further includes a frequency that the predetermined routine is to be repeated.

6. The method of claim 1, wherein the automated fluid sampling device further includes a user interface comprising the single button.

7. The method of claim 6, wherein the automated fluid sampling device further includes a cover covering at least a portion of the user interface.

8. The method of claim 7, wherein the cover covers the single button.

9. The method of claim 7, wherein the cover is flexible.

10. The method of claim 7, wherein the cover is transparent.

11. The method of claim 1, further comprising closing the first valve and second valve, opening the third valve, and moving the pump in the first direction to draw fluid into the pump.

12. The method of claim 11, further comprising opening the second valve and moving the pump in the second direction to expel fluid from the reservoir.

13. The method of claim 1, further comprising closing the first and third valves, opening the second valve, and moving pump in the second direction to expel fluid from the pump.

14. The method of claim 1, wherein the support components are snap and routing supports, and each of the pump, the reservoir, the first fluid conduit, the second fluid conduit, and the third fluid conduit is removably secured to the frame by one of the snap and routing supports.

* * * * *